(12) United States Patent
Hidaka

(10) Patent No.: US 9,943,248 B2
(45) Date of Patent: Apr. 17, 2018

(54) ELECTRONIC DEVICE, CONTROL METHOD, AND CONTROL PROGRAM

(71) Applicant: KYOCERA CORPORATION, Kyoto-shi, Kyoto (JP)

(72) Inventor: Hideki Hidaka, Hino (JP)

(73) Assignee: KYOCERA CORPORATION, Kyoto (JP)

( * ) Notice: Subject to any disclaimer, the term of this patent is extended or adjusted under 35 U.S.C. 154(b) by 160 days.

(21) Appl. No.: 14/410,829

(22) PCT Filed: Jun. 21, 2013

(86) PCT No.: PCT/JP2013/067126
§ 371 (c)(1),
(2) Date: Dec. 23, 2014

(87) PCT Pub. No.: WO2014/002906
PCT Pub. Date: Jan. 3, 2014

(65) Prior Publication Data
US 2015/0182146 A1    Jul. 2, 2015

(30) Foreign Application Priority Data

Jun. 25, 2012 (JP) ................. 2012-142192
Jun. 26, 2012 (JP) ................. 2012-143248

(51) Int. Cl.
| | |
|---|---|
| H04M 3/00 | (2006.01) |
| A61B 5/08 | (2006.01) |
| G01N 33/497 | (2006.01) |
| H04M 1/725 | (2006.01) |
| A61B 5/00 | (2006.01) |

(Continued)

(52) U.S. Cl.
CPC .......... *A61B 5/082* (2013.01); *A61B 5/6898* (2013.01); *G01N 33/497* (2013.01); *H04M 1/72569* (2013.01); *H04M 1/03* (2013.01); *H04M 1/21* (2013.01); *H04M 1/6008* (2013.01)

(58) Field of Classification Search
CPC . G01N 33/497; G01N 33/4972; G01N 2/2244
See application file for complete search history.

(56) References Cited

U.S. PATENT DOCUMENTS

2006/0058697 A1* 3/2006 Mochizuki .......... A61B 5/0002
600/532
2008/0274764 A1* 11/2008 Masuda ................. H04B 1/44
455/550.1

(Continued)

FOREIGN PATENT DOCUMENTS

| JP | 2003-115902 A | 4/2003 |
| JP | 2004-255029 A | 9/2004 |

(Continued)

OTHER PUBLICATIONS

International Search Report dated Aug. 27, 2013, in corresponding International Application No. PCT/JP2013/067126.

*Primary Examiner* — Olumide T Ajibade Akonai
*Assistant Examiner* — Edward Zhang
(74) *Attorney, Agent, or Firm* — Hauptman Ham, LLP

(57) ABSTRACT

According to one of aspects, an electronic device used for a phone call includes: a sound input unit to which a sound is input during a phone call; and a sensor that is provided near the sound input unit and detects a substance contained in a gas.

23 Claims, 28 Drawing Sheets

(51) Int. Cl.
    *H04M 1/21*     (2006.01)
    *H04M 1/03*     (2006.01)
    *H04M 1/60*     (2006.01)

(56) References Cited

U.S. PATENT DOCUMENTS

| | | | | |
|---|---|---|---|---|
| 2009/0309711 | A1* | 12/2009 | Adappa | G06Q 30/02 340/501 |
| 2009/0325639 | A1* | 12/2009 | Koehn | B60K 28/063 455/556.1 |
| 2010/0234064 | A1* | 9/2010 | Harris, Jr. | B60K 28/066 455/556.1 |
| 2011/0054650 | A1* | 3/2011 | Wang | H04M 19/04 700/94 |
| 2012/0252527 | A1* | 10/2012 | Kim | H04M 1/67 455/556.1 |
| 2013/0154797 | A1* | 6/2013 | Lee | G06F 3/002 340/5.74 |
| 2014/0208829 | A1* | 7/2014 | Lechner | G01N 33/497 73/31.01 |
| 2014/0349707 | A1* | 11/2014 | Bang | H04Q 9/00 455/556.1 |

FOREIGN PATENT DOCUMENTS

| | | |
|---|---|---|
| JP | 2005-086405 A | 3/2005 |
| JP | 2005-122673 A | 5/2005 |
| JP | 2007-202174 A | 8/2007 |
| JP | 2010-025718 A | 2/2010 |
| JP | 2010-025720 A | 2/2010 |

* cited by examiner

ELECTRONIC DEVICE, CONTROL METHOD, AND CONTROL PROGRAM

CROSS-REFERENCE TO RELATED APPLICATION

The present application is a National Phase of International Application Number PCT/JP2013/067126 filed on Jun. 21, 2013, and claims the benefit of priority from Japanese Patent Application Nos. 2012-142192 filed on Jun. 25, 2012 and 2012-143248 filed on Jun. 26, 2012.

FIELD

The present application relates to an electronic device having a function of detecting a substance contained in a gas, a control method, and a control program.

BACKGROUND

A technology of detecting a substance contained in a human breath and using a detection result for the purpose of healthcare and the like is known. For example, Patent Literature 1 discloses a breath measurement device for easily collecting a small amount of specific gas component contained in a breath and accurately measuring the concentration of the gas component.

CITATION LIST

Patent Literature

Patent Literature 1: JP-A-2010-025720
Patent Literature 2: JP-A-2005-122673

TECHNICAL PROBLEM

When using the breath measurement device, the user blows on a predetermined part of the breath measurement device. Such an operation for detection of a substance contained in a human breath may be sometimes troublesome for the user. For the foregoing reasons, there is a need for an electronic device having a function of detecting a substance contained in a gas, a control method, and a control program that detect a substance contained in the breath of the user in an unconscious manner.

SUMMARY

According to one of aspects, an electronic device used for a phone call includes: a sound input unit to which a sound is input during a phone call; and a sensor that is provided near the sound input unit and detects a substance contained in a gas.

According to one of aspects, an electronic device used for a phone call includes: a sensor that detects a substance contained in a gas; and a controller that activates the sensor when a phone call function is in execution.

According to one of aspects, a control method is executed by an electronic device used for a phone call. The method includes: determining whether a phone call function is in execution; and activating, when it is determined that the phone call function is in execution, a sensor for detecting a substance contained in a gas According to one of aspects, a control program causes an electronic device used for a phone call to execute: determining whether a phone call function is in execution; and activating, when it is determined that the phone call function is in execution, a sensor for detecting a substance contained in a gas.

DESCRIPTION OF EMBODIMENTS

Exemplary embodiments of the present invention will be explained in detail below with reference to the accompanying drawings. Mobile phones will be explained below as examples of an electronic device having a function of detecting a substance contained in a gas.

Embodiment 1

Figure 1:
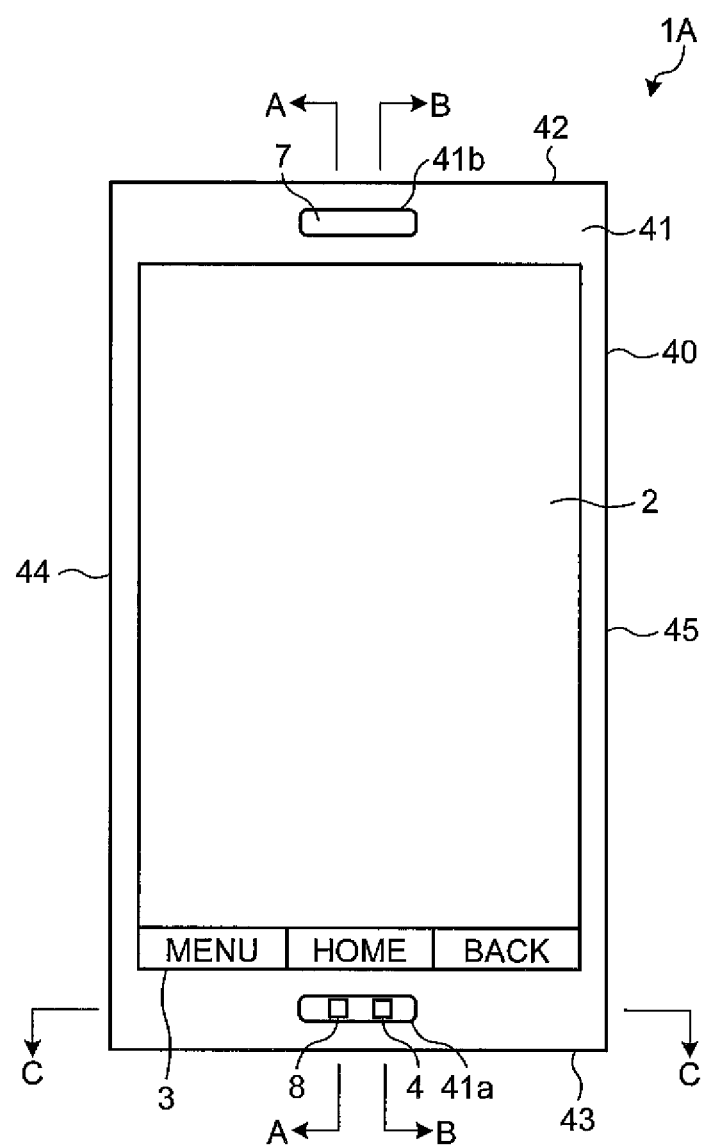
FIG. 1 is a front view of a mobile phone according to Embodiment 1.
Figure 2:
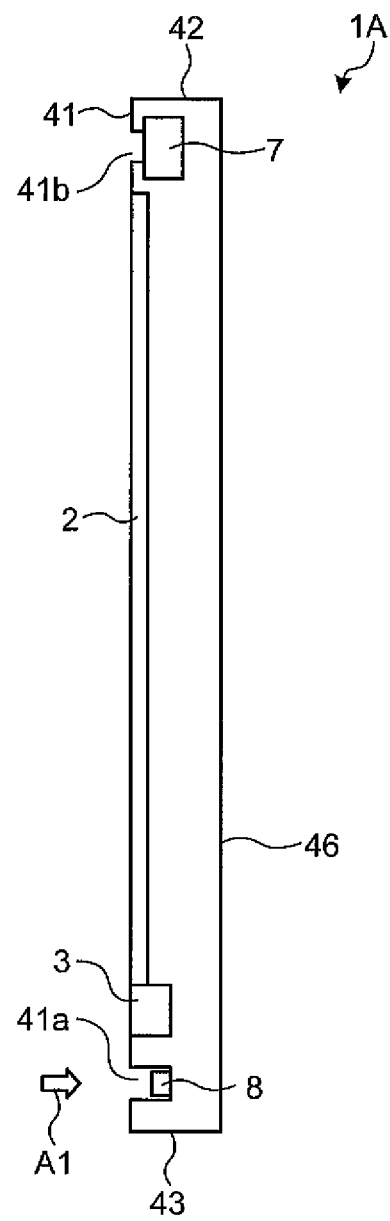
FIG. 2 is an A-A cross section of the mobile phone according to Embodiment 1.
Figure 3:
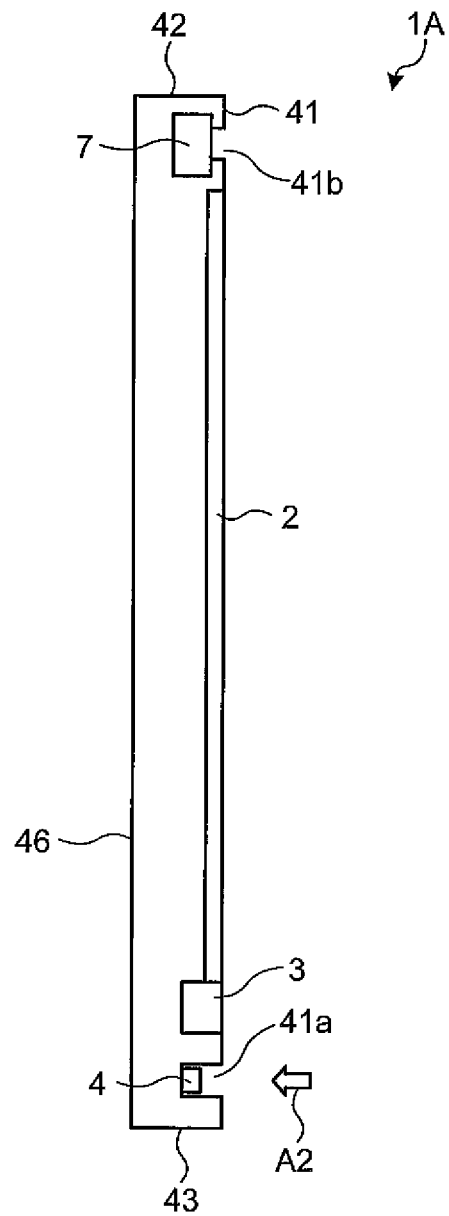
FIG. 3 is a B-B cross section of the mobile phone according to Embodiment 1.
Figure 4:
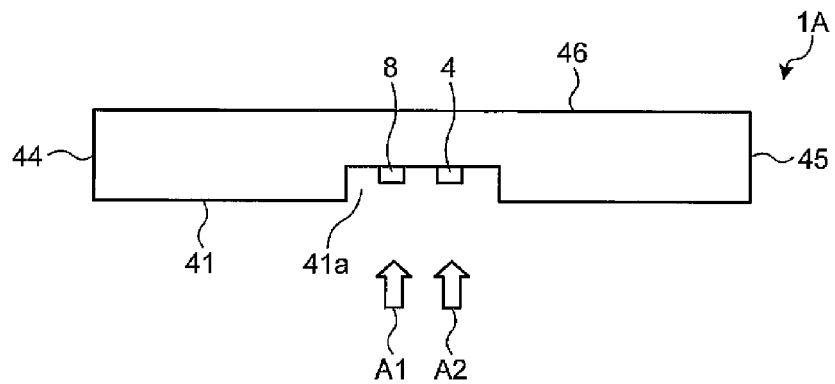
FIG. 4 is a C-C cross section of the mobile phone according to Embodiment 1.
Figure 5:
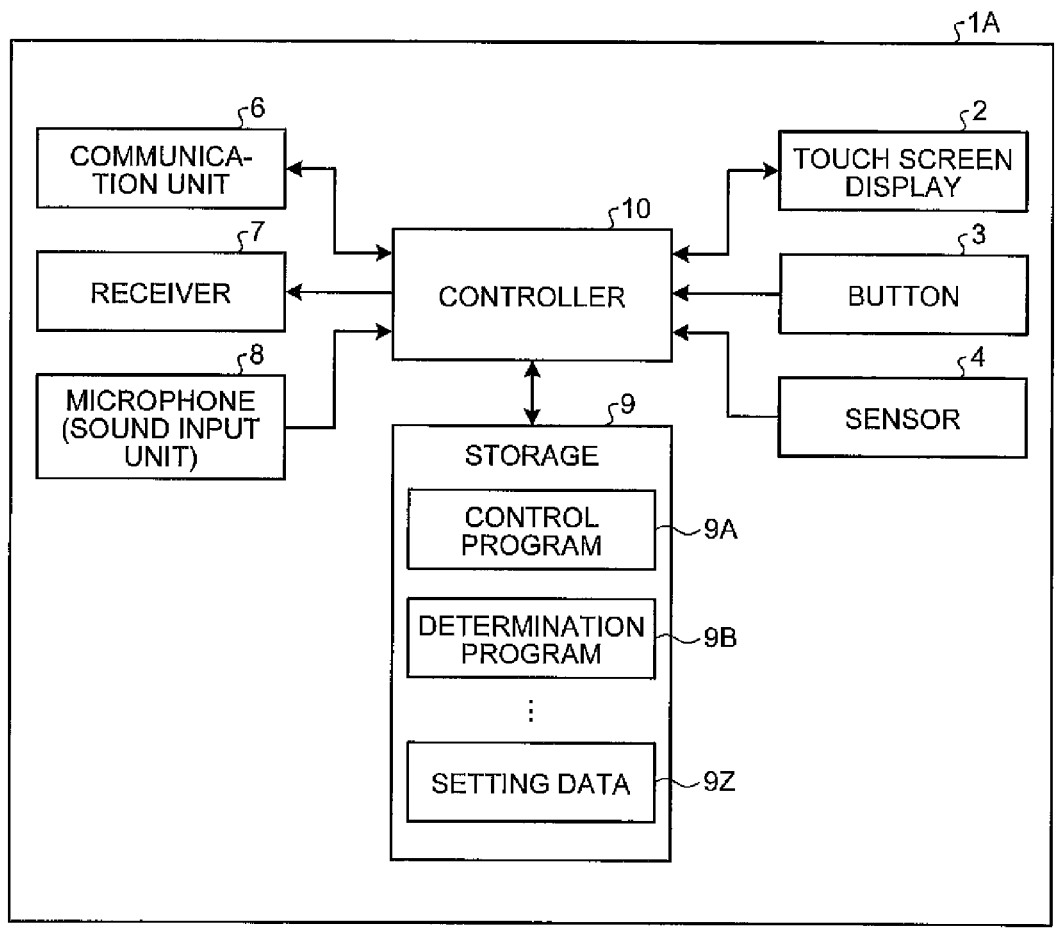
FIG. 5 is a block diagram of the mobile phone according to Embodiment 1.

A configuration of a mobile phone 1A according to Embodiment 1 will be explained below with reference to FIG. 1 to FIG. 5. FIG. 1 is a front view of the mobile phone 1A. FIG. 2 is an A-A cross section of the mobile phone 1A. FIG. 3 is a B-B cross section of the mobile phone 1A. FIG. 4 is a C-C cross section of the mobile phone 1A. FIG. 5 is a block diagram of the mobile phone 1A.

As illustrated in FIG. 1 to FIG. 5, the mobile phone 1A includes a touch screen display 2, buttons 3, a sensor 4, a communication unit 6, a receiver 7, a microphone (sound input unit) 8, a storage 9, a controller 10, and a housing 40. The housing 40 has faces 41 to 46, and various components are supported by the inner sides and the outer sides of the faces.

The touch screen display 2 is provided to the face 41. The touch screen display 2 is provided with a display device such as a liquid crystal display (LCD), an organic electro-luminescence display (OELD), or an inorganic electro-luminescence display (IELD). The display device displays text, images, symbols, graphics, and the like.

The touch screen display 2 is further provided with the touch screen (touch sensor). The touch screen detects contact. The touch screen is used to detect a gesture (contact operation) by a user with a finger, a pen, a stylus pen, or the like. Any technology such as capacitive sensing, resistive sensing, surface acoustic wave (or ultrasonic) sensing, infrared sensing, electromagnetic induction sensing, and load sensing, may be used to allow the touch screen to detect contact. The touch screen display 2 may be a simple display unit without the touch screen.

The buttons 3 accept an operation input by a user. The number of the buttons 3 is not limited to an example illustrated in FIG. 1. The buttons 3 may include buttons in the arrangement of a numeric key pad or in a QWERTY layout, for example.

The sensor 4 detects a substance contained in a gas. The sensor 4 is also called an olfactory sensor, an odor sensor, or an exhalation sensor. Examples of a substance detected by the sensor 4 include various chemical substances. Examples of a substance detected by the sensor 4 include a substance used for, for example, the determination of a degree of bad breath, the determination of drinking, the diagnosis of stress, the early detection of a disease such as a cancer, etc. The substance detected by the sensor 4 may be a substance that cannot be detected via olfaction by human beings or animals. The sensor 4 may be configured to detect a plurality of substances in a selective manner.

The sensor 4 may be a Surface Acoustic Wave (SAW) device. The SAW device has an advantage in power saving and high-integration, and is therefore favorable to be provided to a mobile phone that operates by a battery and the downsizing of which is demanded.

The communication unit 6 performs communication via radio waves. A communication system supported by the communication unit 6 is wireless communication standard. The wireless communication standard includes, for example, a communication standard of cellar phones such as 2G, 3G, and 4G. The communication standard of cellar phones includes, for example, Long Term Evolution (LTE), Wideband Code Division Multiple Access (W-CDMA), CDMA 2000, a Personal Digital Cellular (PDC), a Global System for Mobile Communications (GSM), and a Personal Handy-phone System (PHS). The wireless communication standard further includes, for example, Worldwide Interoperability for Microwave Access (WiMAX), IEEE 802.11, Bluetooth, Infrared Data Association (IrDA), and Near Field Communication (NFC). The communication unit 6 may support one or more communication standards.

The receiver 7 is a sound output unit. The receiver 7 outputs a sound signal transmitted from the controller 10 as a sound. The receiver 7 is used to output the voice of a person on the other side during phone call, for example. The microphone 8 is a sound input unit. The microphone 8 converts an input sound into an electric signal. The microphone 8 is used to input the voice of a user during phone call, for example.

The storage 9 stores therein programs and data. The storage 9 is used also as a work area that temporarily stores a processing result of the controller 10. The storage 9 may include any non-transitory storage medium such as a semiconductor storage medium and a magnetic storage medium. The storage 9 may include a plurality type of storage mediums. The storage 9 may include a combination of a portable storage medium such as a memory card, an optical disc, or a magneto-optical disc with a reader of the storage medium. The storage 9 may include a storage device used as a temporary storage area such as Random Access Memory (RAM).

The storage 9 stores, for example, a control program 9A, a determination program 9B, and setting data 9Z. The control program 9A provides functions used to implement basic operations of the mobile phone 1A. Examples of the functions provided by the control program 9A include a function of controlling the sensor 4 to detect a substance contained in a gas. The determination program 9B includes a function of performing various types of determination processing based on the substance detected by the sensor 4. Examples of the determination processing performed by the function provided by the determination program 9B include processing for the determination of a degree of bad breath, the determination of drinking, the diagnosis of stress, the early detection of disease such as a cancer, etc. The setting data 9Z includes information related to various settings related to the operations of the mobile phone 1A.

The controller 10 is a processing unit. Examples of the processing units include, but are not limited to, a Central Processing Unit (CPU), System-on-a-chip (SoC), a Micro Control Unit (MCU), and a Field-Programmable Gate Array (FPGA). The controller 10 integrally controls the operations of the mobile phone 1A to implement various functions.

Specifically, the controller 10 executes instructions contained in the program stored in the storage 9 while referring to the data stored in the storage 9 as necessary. The controller 10 then controls a function unit according to the data and the instructions to thereby implement the various functions. Examples of the function unit include, but are not limited to, the touch screen display 2, the communication unit 6, and the receiver 7. The controller 10 can change the control according to the detection result of a detector. Examples of the detector include, but are not limited to, the touch screen display 2, the buttons 3, the sensor 4, and the microphone 8.

The controller 10 controls the sensor 4 by executing the control program 9A to implement the function of detecting a substance contained in a gas, for example.

In the present embodiment, the face 41 is provided with an opening 41a and an opening 41b. The opening 41a is provided to capture a voice of the user during a phone call. The opening 41b is provided to output a voice of a call partner to the outside during the phone call. Therefore, the opening 41a and the opening 41b are provided such that one of them is provided in one end of the face 41 and the other one is provided in the other end thereof, so that the opening 41a is located near a user's mouth and the opening 41b is located near a user's ear during the phone call.

The receiver 7 is provided inside the opening 41b. The receiver 7 is provided in a direction in which a voice to be output is discharged to the outside through the opening 41b.

The sensor 4 and the microphone 8 are closely provided inside the opening 41a. The sensor 4 is provided in a direction in which a substance contained in a gas introduced from the opening 41a is adequately detected. Specifically, the sensor 4 is provided in a direction in which a substance contained in the gas introduced in a direction indicated by arrow A2 is adequately detected. The microphone 8 is provided in a direction in which a voice transmitted through the opening 41a is adequately detected. Specifically, the microphone 8 is provided in a direction in which a voice transmitted in a direction indicated by arrow A1, which is parallel to the arrow A2, is adequately detected.

In this way, the sensor 4 is provided near the microphone 8. Furthermore, the sensor 4 and the microphone 8 are provided at positions opposite to the opening 41a. Therefore, when the user brings the opening 41a to a portion near his/her mouth so that the microphone 8 can easily capture the voice during the phone call, the breath of the user reaches the sensor 4 as well as the microphone 8. As a result, the substance contained in the breath of the user is detected by the sensor 4.

Based on the configuration, when a phone conversation is performed, the mobile phone 1A can detect a substance contained in the breath of the user and use the detected substance for various types of determination even if the user does not perform any particular operation other than the operation for making a phone call. In other words, the mobile phone 1A can detect a substance contained in the breath of the user in a noninvasive and unconscious manner.

The configuration to obtain the above effects is not limited to the configuration illustrated in FIG. 1 to FIG. 4. More generally, to obtain the effects, it is only necessary that the sensor 4 is provided near the microphone 8. The microphone 8 is not necessarily provided to the same face as that of the receiver 7.

Figure 6:
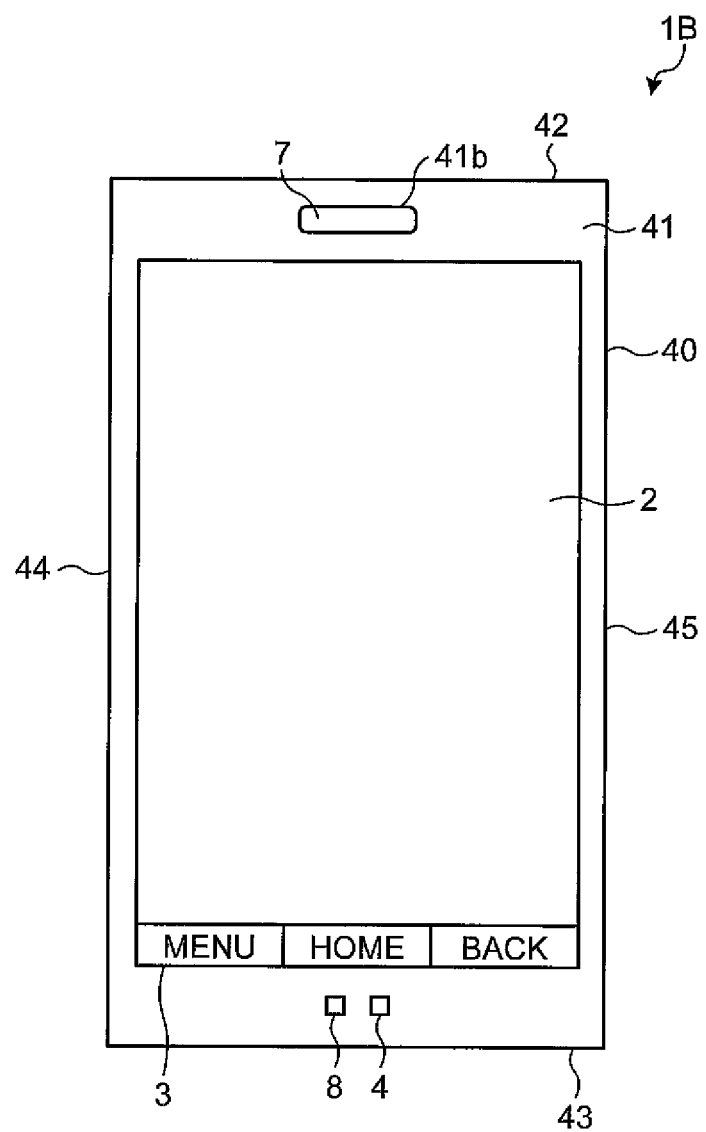
FIG. 6 is a front view of a mobile phone according to a first modification.
Figure 7:
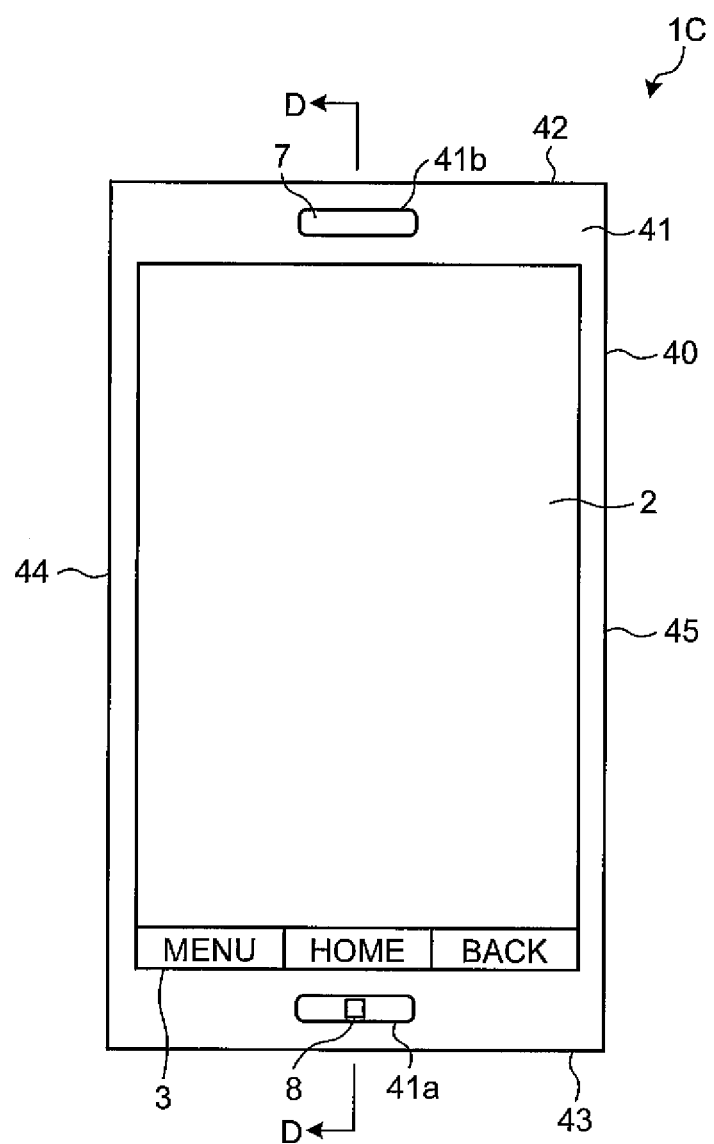
FIG. 7 is a front view of a mobile phone according to a second modification.
Figure 8:
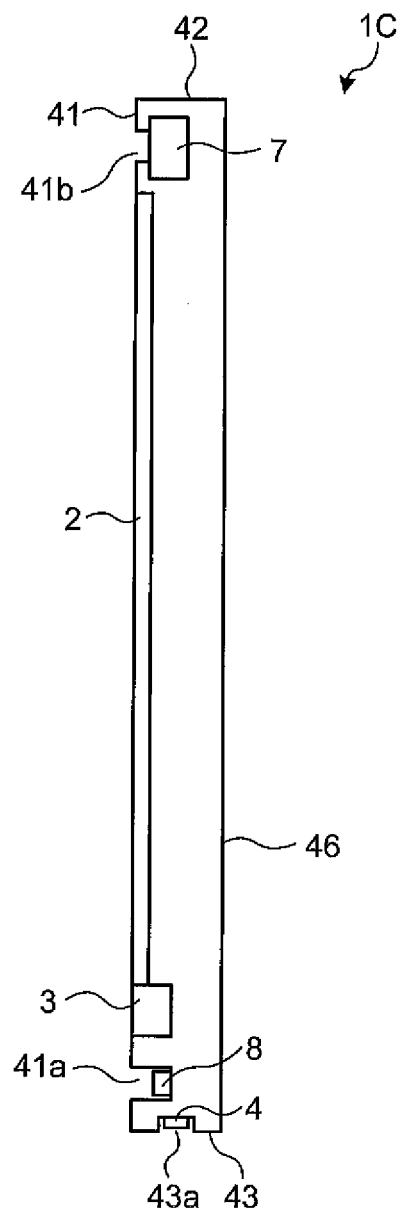
FIG. 8 is a D-D cross section of the mobile phone according to the second modification.

Modes in which the sensor 4 is provided near the microphone 8 will be explained below with reference to FIG. 1 to FIG. 4 and FIG. 6 to FIG. 8. FIG. 6 is a front view of a mobile phone 1B according to a first modification. FIG. 7 is a front view of a mobile phone 1C according to a second modification. FIG. 8 is a D-D cross section of the mobile phone 1C.

The modes in which the sensor 4 is provided near the microphone 8 include modes in which the sensor 4 is provided to any one of the faces of the electronic device on the side where the microphone 8 is provided. The modes in which the sensor 4 is provided on the side where the microphone 8 is provided include a mode in which the sensor 4 and the microphone 8 are provided to an inner side of the face as illustrated in FIG. 1 to FIG. 4. Furthermore, the modes in which the sensor 4 is provided on the side where the microphone 8 is provided include a mode in which the sensor 4 and the microphone 8 are provided to an outer side of the face as is the mobile phone 1B illustrated in FIG. 6.

The microphone 8 may be provided to a face of a substrate stored inside the housing 40. In this case, the modes in which the sensor 4 is provided on the side where the microphone 8 is provided include modes in which the sensor 4 is provided to a face of the substrate on the side where the microphone 8 is provided. When the microphone 8 is provided to the face of the substrate stored inside the housing 40, for a face of the housing 40 opposite to the face of the substrate where the microphone 8 is provided, an opening is formed at a position on the face of the housing 40 that faces the microphone 8.

When the sensor 4 is provided on the side where the microphone 8 is provided, the sensor 4 and the microphone 8 may be arranged so as to be adjacent to each other. A space between the sensor 4 and the microphone 8 may be or may not be formed. When a space is formed between the sensor 4 and the microphone 8, a distance between the sensor 4 and the microphone 8 may be determined according to a sensitivity of the sensor 4.

As already explained, the microphone 8 may be provided to an end apart from the receiver 7 in order to facilitate a phone conversation. In this case, the modes in which the sensor 4 is provided near the microphone 8 include the modes in which the sensor 4 is provided to the end where the microphone 8 is provided, as illustrated in FIG. 1 to FIG. 4. Furthermore, the modes, in this case, where the sensor 4 is provided near the microphone 8 include a mode in which the sensor 4 is provided to another face adjacent to the end where the microphone 8 is provided as is the mobile phone 1C illustrated in FIG. 7 and FIG. 8. The sensor 4 may be provided inside an opening 43a which is provided to another face adjacent to the end where the microphone 8 is provided.

In the mobile phone 1C, the microphone 8 is provided to the end of the face 41, and the sensor 4 is provided to the face 43 adjacent to the face 41 in this end. Even in this mode, the breath of the user during a phone call reaches the sensor 4 as well as the microphone 8. Particularly, in the case of a comparatively small-sized mobile phone, when the user brings the receiver close to his/her ear in order to listen to the voice of the call partner, the bottom face farthest from the receiver can be located nearest to the user's mouth as is the face 43 of the faces. In this case, by providing the sensor 4 to the bottom face, a substance contained in the breath of the user can be effectively detected during the phone call.

When the sensor 4 is configured by combining a plurality of different sensors, the sensor 4 may be provided so that a less sensitive sensor is provided closer to the microphone 8. By providing the sensors in this way, the respective sensors can appropriately detect a substance contained in the breath produced when the user outputs a voice toward the microphone 8.

As explained above, in Embodiment 1, the sensor 4 for detecting a substance contained in the gas is provided to a position that the breath of the user reaches during the phone call. Therefore, the electronic device according to the present embodiment can detect a substance contained in the breath of the user in a noninvasive and unconscious manner during the phone call.

Embodiment 2

Figure 9:
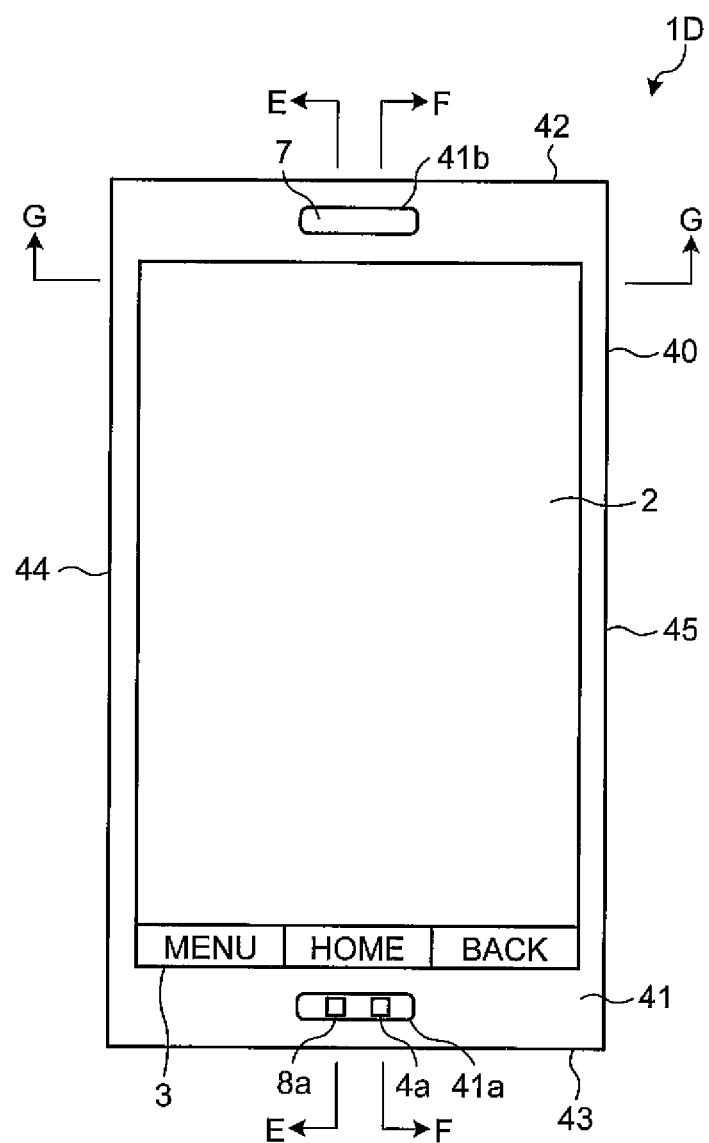
FIG. 9 is a front view of a mobile phone according to Embodiment 2.
Figure 10:
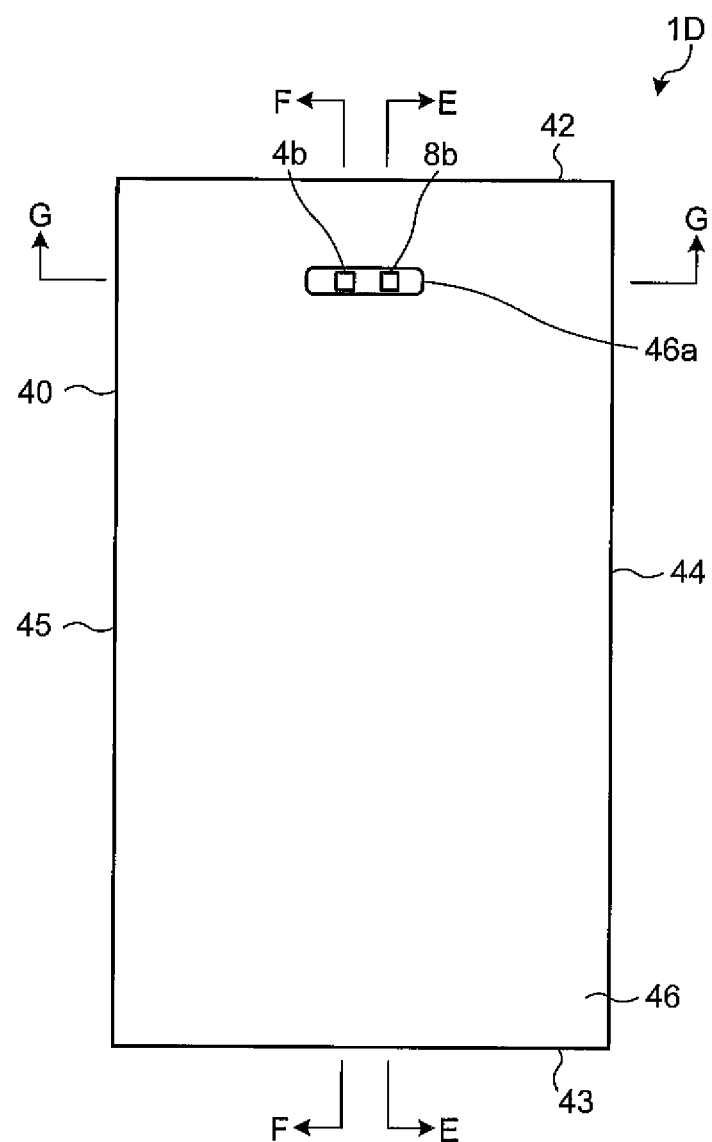
FIG. 10 is a back view of the mobile phone according to Embodiment 2.
Figure 11:
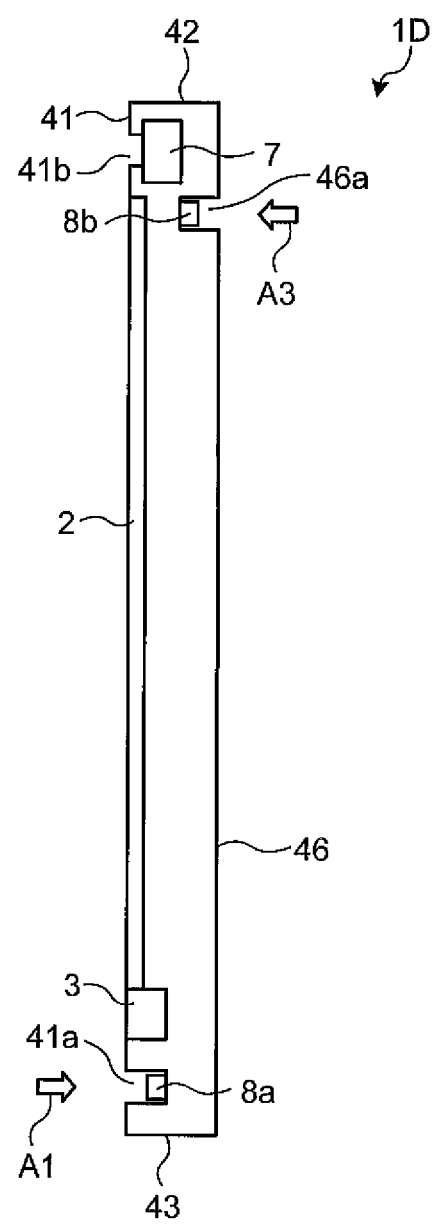
FIG. 11 is an E-E cross section of the mobile phone according to Embodiment 2.
Figure 12:
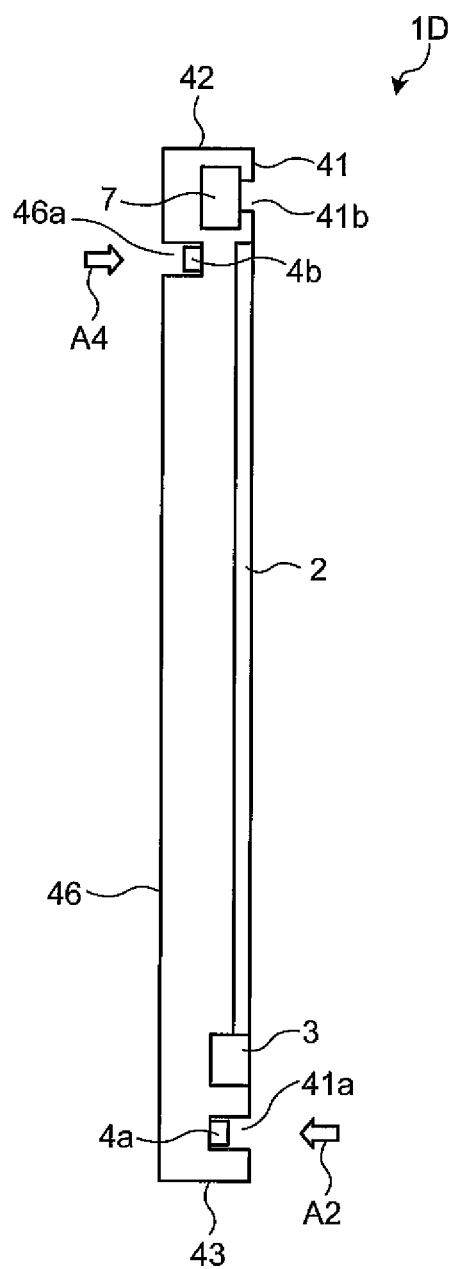
FIG. 12 is an F-F cross section of the mobile phone according to Embodiment 2.
Figure 13:
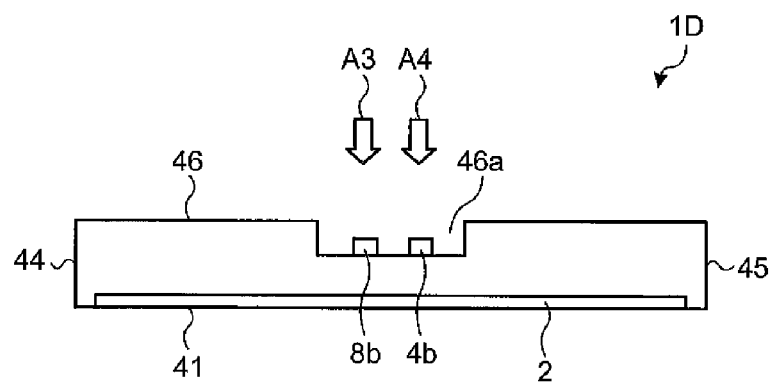
FIG. 13 is a G-G cross section of the mobile phone according to Embodiment 2.
Figure 14:
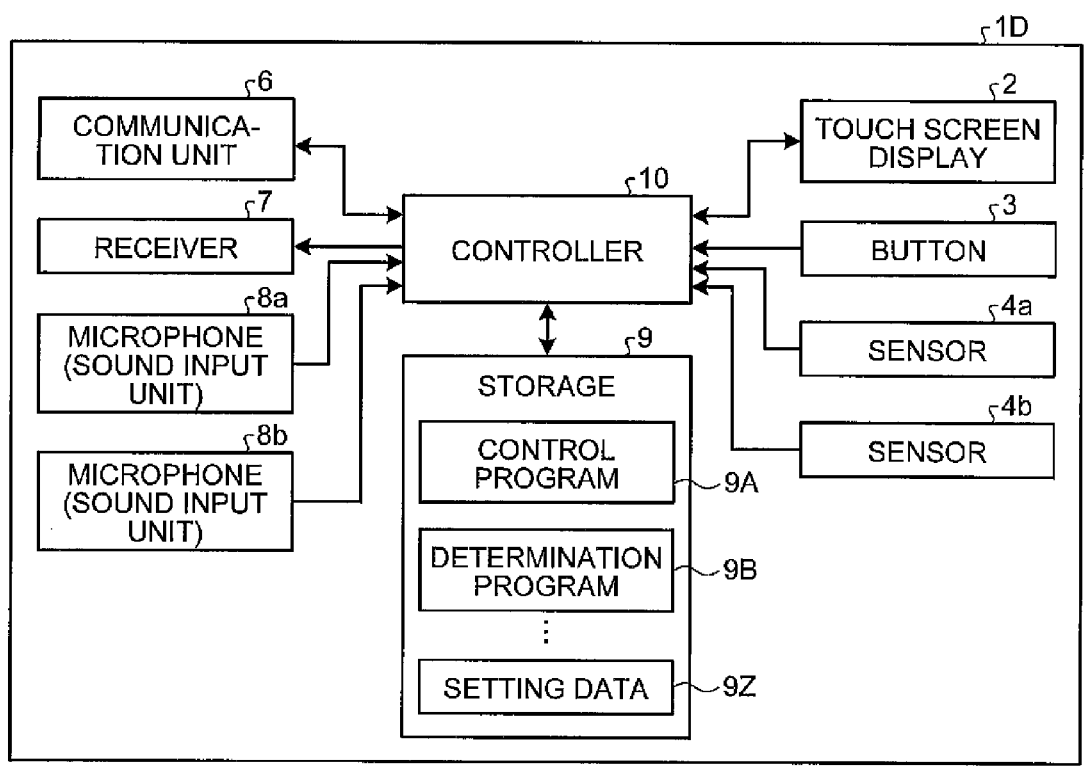
FIG. 14 is a block diagram of the mobile phone according to Embodiment 2.

A configuration of a mobile phone 1D according to Embodiment 2 will be explained below with reference to FIG. 9 to FIG. 14. FIG. 9 is a front view of the mobile phone 1D. FIG. 10 is a back view of the mobile phone 1D. FIG. 11 is an E-E cross section of the mobile phone 1D. FIG. 12 is an F-F cross section of the mobile phone 1D. FIG. 13 is a G-G cross section of the mobile phone 1D. FIG. 14 is a block diagram of the mobile phone 1D. In the following explanation, the same reference signs as these used for the already explained portions may be assigned to portions the same as the already explained portions. In the following explanation, explanation overlapping the already explained one may be omitted.

As illustrated in FIG. 9 to FIG. 14, the mobile phone 1D includes the touch screen display 2, the button 3, a sensor 4a, a sensor (second sensor) 4b, the communication unit 6, the receiver 7, a microphone (sound input unit) 8a, a microphone (sound input unit) 8b, the storage 9, the controller 10, and the housing 40.

The sensors 4a and 4b are the sensor similar to the sensor 4. That is, the sensors 4a and 4b detect a substance contained in the gas. The microphones 8a and 8b are the sound input unit similar to the microphone 8. That is, the microphones 8a and 8b convert an input sound into an electric signal.

The face 41 of the housing 40 is provided with the opening 41a and the opening 41b. The opening 41a is provided to capture a voice of the user during a phone call. The opening 41b is provided to output a voice of the call partner to the outside during the phone call. Therefore, the opening 41a and the opening 41b are provided such that one of them is provided in one end of the face 41 and the other one is provided in the other end thereof, so that the opening 41a is located near the user's mouth and the opening 41b is located near a user's ear during the phone call.

The receiver 7 is provided inside the opening 41b. The receiver 7 is provided in a direction in which a voice to be output is discharged to the outside through the opening 41b.

The sensor 4a and the microphone 8a are closely provided inside the opening 41a. The sensor 4a is provided in a direction in which a substance contained in the gas introduced from the opening 41a is adequately detected. Specifically, the sensor 4a is provided in a direction in which a substance contained in the gas introduced in the direction indicated by the arrow A2 is adequately detected. The microphone 8a is provided in a direction in which a voice transmitted through the opening 41a is adequately detected. Specifically, the microphone 8a is provided in a direction in which a voice transmitted in a direction indicated by the arrow A1, which is parallel to the arrow A2, is adequately detected.

The housing 40 has a face 46 on the opposite side of the face 41. The face 46 is provided with an opening 46a. In the following explanation, the face 41 may be called a front face and the face 46 may be called a back face. The opening 46a is provided to a position less likely to be covered by the hand holding the mobile phone 1D during a phone call.

A sensor 4b and a microphone 8b are closely provided inside the opening 46a. The sensor 4b is provided in a direction in which a substance contained in the gas introduced from the opening 46a is adequately detected. Specifically, the sensor 4b is provided in a direction in which a substance contained in the gas introduced in the direction indicated by arrow A4 is adequately detected. The microphone 8b is provided in a direction in which a voice transmitted through the opening 46a is adequately detected. Specifically, the microphone 8b is provided in a direction in which a voice transmitted in a direction indicated by arrow A3, which is parallel to the arrow A4, is adequately detected.

The microphone 8b is used to acquire sounds around the mobile phone 1D during a phone call. The controller 10 uses the sounds acquired by the microphone 8b for noise cancellation. Specifically, the controller 10 inverses a sound signal input through the microphone 8b and superimposes the inverted sound signal on a sound signal input through the microphone 8a during the phone call. Such a control allows removal of components of the sounds around the mobile phone 1D from the sound signal transmitted to the call partner.

The sensor 4b is used to detect a substance contained in the gas around the mobile phone 1D. The controller 10 uses a detection result of the sensor 4b to remove influence of the substance contained in the gas around the mobile phone 1D from a detection result of the sensor 4a. Specifically, the controller 10 determines the concentration or the like of the substance contained in the breath of the user, during the phone call, based on a value obtained by subtracting a detected value of the sensor 4b from a detected value of the sensor 4a.

Figure 15:
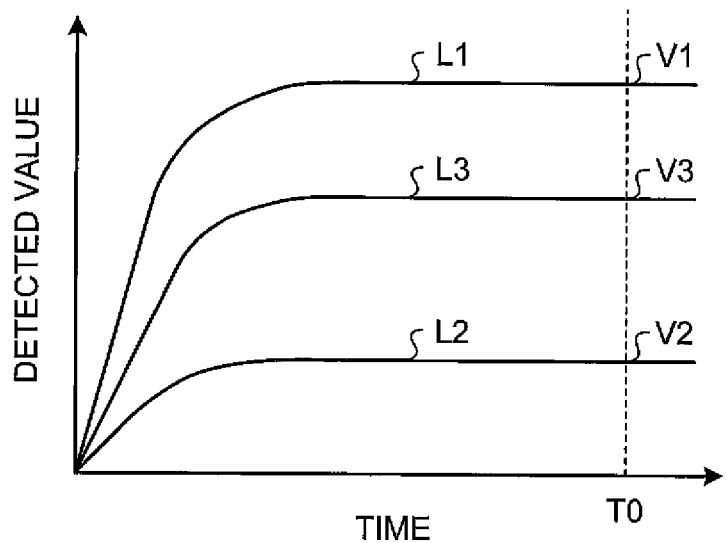
FIG. 15 is a diagram of a detection example of a substance contained in a gas.

How to detect a substance according to Embodiment 2 will be explained in more detail below with reference to FIG. 15. FIG. 15 is a diagram of a detection example of a certain substance (hereinafter, "substance A") contained in a gas. When the controller 10 turns on the sensor 4a at the time of a phone call, a detected value of the substance A indicated by the sensor 4a changes like, for example, line L1. At this time, the controller 10 further turns on the sensor 4b. When the substance A is originally contained in the gas around the mobile phone 1D, a detected value of the substance A indicated by the sensor 4b changes like, for example, line L2.

The gas in which the substance A is detected by the sensor 4a is a gas in which the breath of the user and the gas around the mobile phone 1D are mixed. When the substance A is originally contained in a gas (second gas) around the mobile phone 1D, the detected value of the sensor 4a includes the influence of the gas around the mobile phone 1D. Therefore, the controller 10 subtracts the detected value of the sensor 4b from the detected value of the sensor 4a. For example, the controller 10 uses a detected value V3, obtained by subtracting a detected value V2 of the sensor 4b after T0 seconds since turning-on from a detected value V1 of the sensor 4a after T0 seconds since turning-on, for various types of determination processing, as a concentration of the substance A contained in the breath of the user. In the example illustrated in FIG. 15, a detected value obtained by subtracting the detected value of the sensor 4b from the detected value of the sensor 4a changes like line L3.

Figure 16:
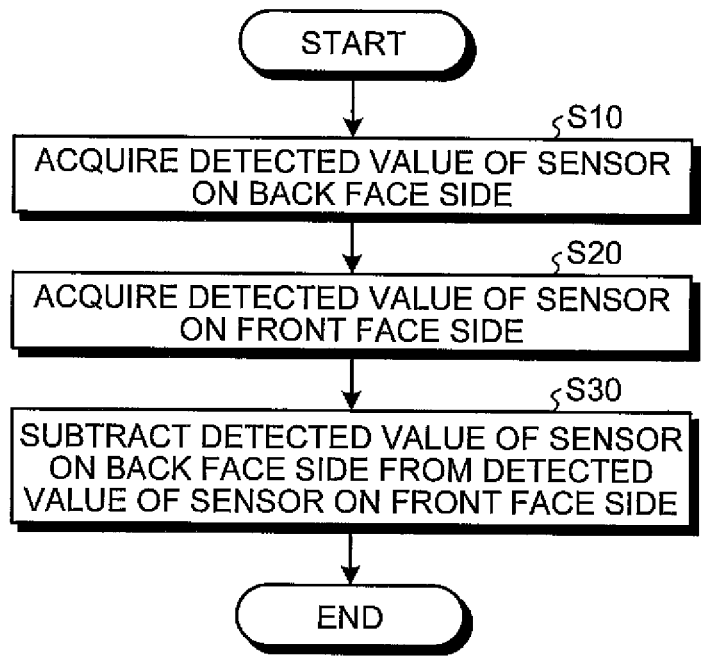
FIG. 16 is a flowchart of a processing procedure of detection processing of the substance.

A processing procedure of detection processing of a substance according to Embodiment 2 will be explained below with reference to FIG. 16. FIG. 16 is a flowchart of a processing procedure of the detection processing of the substance. The processing procedure illustrated in FIG. 16 is executed during a phone call. The sensors 4a and 4b are turned on before the processing procedure illustrated in FIG. 16. When the sensors 4a and 4b are used to detect a plurality of substances, the processing procedure illustrated in FIG. 16 is executed for each substance.

At Step S10, the controller 10 acquires a detected value of the sensor 4b on the back face side. At Step S20, the controller 10 acquires a detected value of the sensor 4a on the front face side. An execution sequence of Steps S10 and S20 may be reversed. Then, at Step S30, the controller 10 subtracts the detected value of the sensor 4b from the detected value of the sensor 4a.

In this way, the detection of the substance contained in the gas around the mobile phone 1D enables the detection accuracy of the substance contained in the breath of the user to be improved. However, during the phone call, the voice uttered by the user causes the substance contained in the breath of the user to spread in the gas around the mobile phone 1D. To reduce the influence of such spread, the sensor for detecting a substance contained in the ambient gas may be provided to a face different from the face where the sensor for detecting the substance contained in the breath is provided. Furthermore, as illustrated in FIG. 9 to FIG. 13, the sensor for detecting a substance contained in the ambient gas may be provided to a face opposite to the face where the sensor for detecting the substance contained in the breath is provided.

The arrangement of the sensor 4a and the microphone 8a may be appropriately changed as is the arrangement of the sensor 4 and the microphone 8. The sensor 4b does not need to be provided close to the microphone 8b. The mobile phone 1D does not need to have a noise cancelling function during a phone call. That is, the mobile phone 1D does not have to include the microphone 8b.

As explained above, by using the sensors provided to the different faces, it is possible to detect a substance contained in the breath of the user with higher accuracy while maintaining the noninvasive and unconscious manner.

The embodiments disclosed in the present application can include items obvious to those skilled in the art, and can be modified in a range without departing the gist and the scope of the invention. Furthermore, the embodiments and modifications thereof disclosed in the present application can be appropriately combined with each other. For example, the embodiments may be modified as follows.

The sensor 4 may be configured as a component integrated with the microphone 8. The sensor 4a may be configured as a component integrated with the microphone 8a. In this way, by configuring the sensor as a component integrated with the microphone, it is ensured that the sensor is provided close to the microphone. Moreover, for example, when a plurality of sensors for respectively detecting specific substances are arranged around the microphone, it is possible to detect various substances contained in the breath during the phone call while saving a space.

The embodiments have explained the examples of detecting substances contained in the breath of the user during the phone call; however, the timing of detecting the substance contained in the breath of the user is not limited thereto. The timing of detecting each substance contained in the breath of the user by using a sensor provided near the microphone has only to be a timing when the user outputs a voice near the microphone. Examples of the timing when the user outputs a voice near the microphone include a timing when an instruction is issued by voice input and a timing when a voice is recorded.

Recently, research and development to apply a technology of measuring a causative substance of odor to various industrial fields have been advanced, and practical use of the technology is already started in many industrial fields. For example, Patent Literature 2 discloses a system for measuring an amount of alcohol contained in a breath of a user by using a device connected to a mobile phone carried by the user for the purpose of preventing drunk driving. In a medical field, a device or the like for detecting the presence of Helicobacter pylori based on the concentration of carbon dioxide contained in the breath is put into the practical use.

Embodiment 3

Incidentally, a wide variety of functions are provided in a mobile phone, and power consumption associated with the functions becomes a problem. If a function of measuring a causative substance of odor or the like as data for the user is provided in a mobile phone, a system of acquiring measurement data while achieving power saving is required.

For the foregoing reasons, there is a need for an electronic device, a control method, and a control program capable of reducing, as much as possible, the power consumed when the data for the user is measured.

Figure 17:
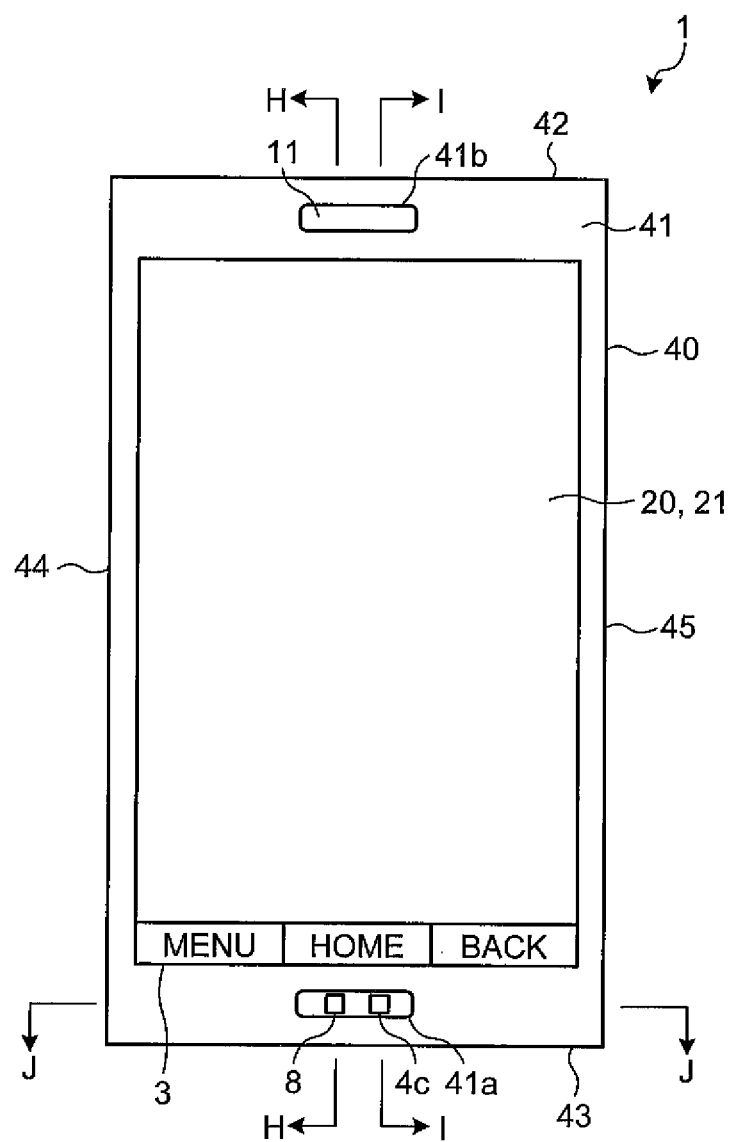
FIG. 17 is a front view of a mobile phone according to Embodiment 3.
Figure 18:
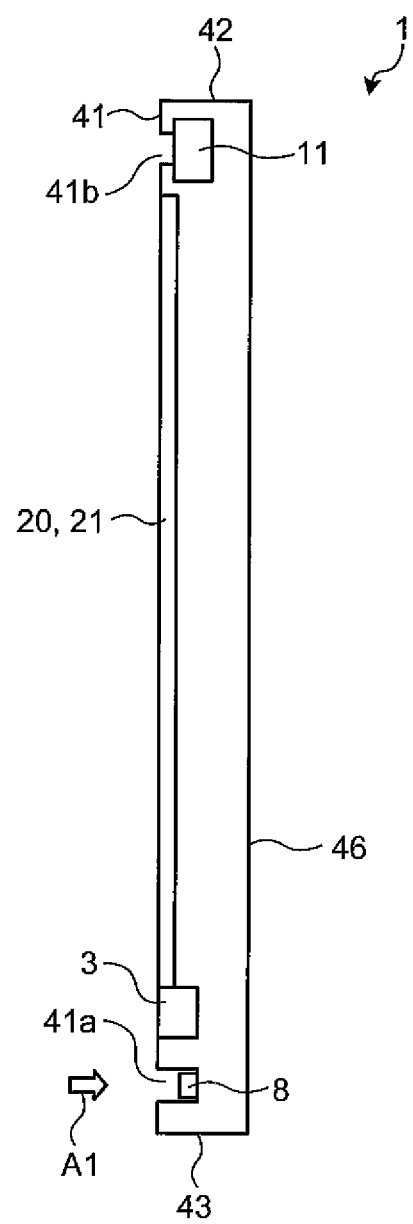
FIG. 18 is an H-H cross section of the mobile phone according to Embodiment 3.
Figure 19:
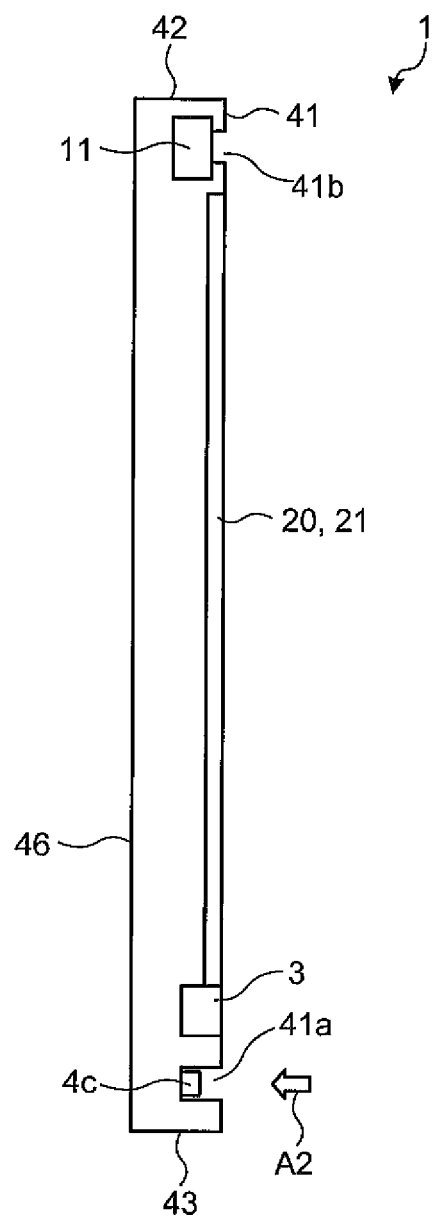
FIG. 19 is an I-I cross section of the mobile phone according to Embodiment 3.
Figure 20:
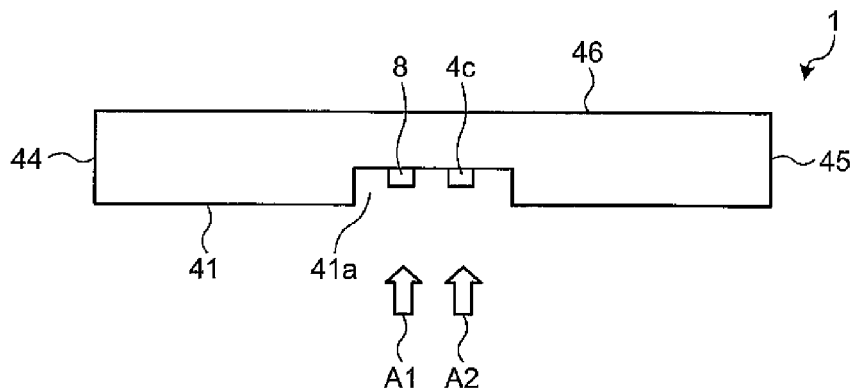
FIG. 20 is a J-J cross section of the mobile phone according to Embodiment 3.

A physical configuration of a mobile phone according to an embodiment explained below will be explained with reference to FIG. 17 to FIG. 20. FIG. 17 is a front view of a mobile phone 1 according to Embodiment 3. FIG. 18 is an H-H cross section of the mobile phone 1 according to Embodiment 3. FIG. 19 is an I-I cross section of the mobile phone 1 according to Embodiment 3. FIG. 20 is a J-J cross section of the mobile phone 1 according to Embodiment 3.

As illustrated in FIG. 17 to FIG. 20, the mobile phone 1 includes the housing 40. The housing 40 has the faces 41 to 46, and various components are supported by the inner sides and the outer sides of the faces. The face 41 of the mobile phone 1 is provided with the opening 41a and the opening 41b. The opening 41a is provided to capture a voice of the user during a phone call. The opening 41b is provided to output a voice of the call partner to the outside during the phone call. Therefore, the opening 41a and the opening 41b are provided such that one of them is provided in one end of the face 41 and the other one is provided in the other end thereof, so that the opening 41a is located near the user's mouth and the opening 41b is located near a user's ear during the phone call.

A speaker 11 is provided inside the opening 41b. The speaker 11 is provided in a direction in which a voice to be output is discharged to the outside through the opening 41b. The speaker 11 may be called a receiver when it is mainly used for outputting the voice during the phone call.

An olfactory sensor 4c and the microphone 8 are closely provided inside the opening 41a, as illustrated in, for example, FIG. 20. The olfactory sensor 4c is provided in a direction in which a substance contained in the gas introduced from the opening 41a is adequately detected. Specifically, as illustrated in FIG. 19 and FIG. 20, the olfactory sensor 4c is provided in a direction in which a substance contained in the gas introduced in a direction indicated by arrow A2 is adequately detected. The microphone 8 is provided in a direction in which a voice transmitted through the opening 41a is adequately detected. Specifically, as illustrated in FIG. 18 and FIG. 20, the microphone 8 is provided in a direction in which a voice transmitted in a direction indicated by the arrow A1, which is parallel to the arrow A2, is adequately detected.

In this way, the olfactory sensor 4c is provided near the microphone 8. Furthermore, the olfactory sensor 4c and the microphone 8 are provided at positions opposite to the opening 41a. Therefore, when the user brings the opening 41a to a portion near his/her mouth so that the microphone 8 can easily capture the voice during the phone call, the breath of the user reaches the olfactory sensor 4c as well as the microphone 8. As a result, the substance contained in the breath of the user is detected by the olfactory sensor 4c.

Based on the configuration, when a phone call is made, the mobile phone 1 can detect a substance contained in the breath of the user and use the detected substance for various types of determination even if the user does not perform any particular operation other than the operation for making a phone call. In other words, the mobile phone 1 can detect a substance contained in the breath of the user in a noninvasive and unconscious manner.

The configuration to obtain the above effects is not limited to the configuration illustrated in FIG. 17 to FIG. 20. More generally, it is only necessary that at least the olfactory sensor 4c is provided near the microphone 8.

Figure 21:
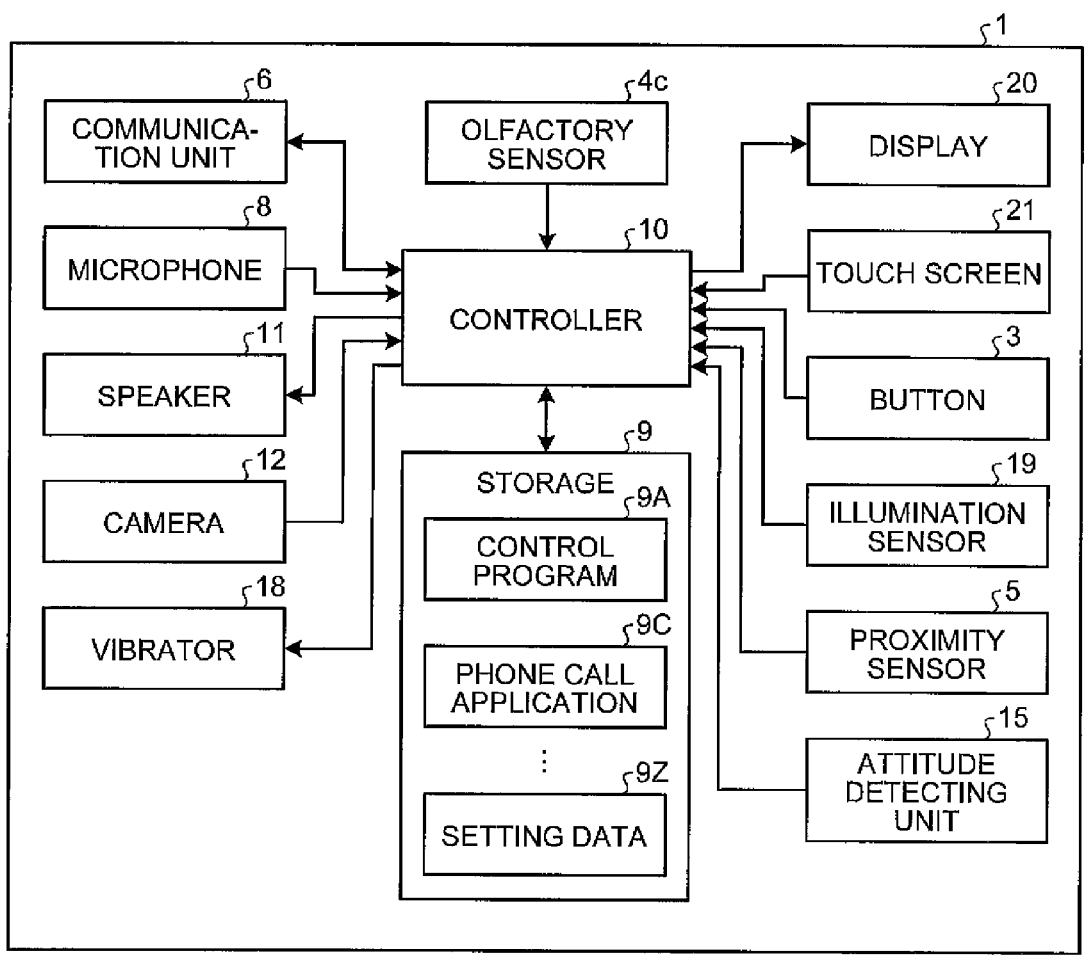
FIG. 21 is a block diagram of the mobile phone according to Embodiment 3.

A functional configuration of the mobile phone according to Embodiment 3 will be explained with reference to FIG. 21. FIG. 21 is a block diagram of the mobile phone according to Embodiment 3. As illustrated in FIG. 21, the mobile phone 1 includes a display 20, the buttons 3, the olfactory sensor 4c, a proximity sensor 5, the communication unit 6, the microphone 8, the storage 9, the controller 10, the speaker 11, a camera 12, an attitude detection unit 15, a vibrator 18, an illumination sensor 19, and a touch screen 21.

The display 20 is provided with a display device such as a liquid crystal display (LCD), an organic electroluminescence display (GELD), or an inorganic electroluminescence display (IELD). The display 22 displays text, images, symbols, graphics, and the like.

The buttons 3 accept an operation input by a user. The number of the buttons 3 may be single or plural.

The illumination sensor 19 detects illuminance of the ambient light of the mobile phone 1. The illuminance indicates intensity of light, lightness, or brightness. The illumination sensor 19 is used, for example, to adjust the brightness of the display 20.

The proximity sensor 5 detects the presence of a nearby object without any physical contact. The proximity sensor 5 detects the presence of the object based on a change of the magnetic field, a change of the return time of the reflected ultrasonic wave, etc. The proximity sensor 5 detects that, for example, the display 20 is brought close to someone's face. The illumination sensor 19 and the proximity sensor 5 may be configured as one sensor. The illumination sensor 19 can be used as a proximity sensor.

The communication unit 6 performs communication via radio waves. A communication system supported by the communication unit 6 is wireless communication standard. The wireless communication standard includes, for example, a communication standard of cellar phones such as 2G, 3G, and 4G. The communication standard of cellar phones includes, for example, Long Term Evolution (LTE), Wideband Code Division Multiple Access (W-CDMA), CDMA 2000, a Personal Digital Cellular (PDC), a Global System for Mobile Communications (GSM), and a Personal Handy-phone System (PHS). The wireless communication standard further includes, for example, Worldwide Interoperability for Microwave Access (WiMAX), IEEE 802.11, Bluetooth, Infrared Data Association (IrDA), and Near Field Communication (NFC), and Wireless Personal Area network (WPAN). The communication standard of WPAN includes, for example, ZigBee. The communication unit 6 may support one or more communication standards.

The olfactory sensor 4c detects a substance contained in a gas. For example, the olfactory sensor 4c measures a concentration of a specific substance contained in a gas. The olfactory sensor 4c is also called an odor sensor or an exhalation sensor. Examples of a substance detected by the olfactory sensor 4c include various chemical substances. Examples of a substance detected by the olfactory sensor 4c includes a substance used for, for example, the determination of a degree of bad breath, the determination of drinking, the diagnosis of stress, the early detection of a disease such as a cancer, etc. The substance detected by the olfactory sensor 4c may be a substance that cannot be detected via olfaction by human beings but can be detected via olfaction by, for example, a dog. The olfactory sensor 4c may be configured to detect a plurality of substances in a selective manner. The olfactory sensor 4c may transmit a detection result of the substance contained in the gas to the controller 10 or may transmit measurement data such as the concentration of the specific substance contained in the gas to the controller 10. When the configuration is such that the measurement data is transmitted from the olfactory sensor 4c to the controller 10, the controller 10 detects and determines the substance.

The olfactory sensor 4c may be a Surface Acoustic Wave (SAW) device. The SAW device has an advantage in power saving and high-integration, and is therefore favorable to be provided to a mobile phone that operates by a battery and the downsizing of which is demanded.

The microphone 8 is a sound input unit. The microphone 8 converts an input sound into an electric signal, and transmits the electric sound to the controller 10. When a voice produced by a user is input, for example, during phone call, the microphone 8 transmits a sound pressure level of a sound signal to the controller 10.

The storage 9 stores therein programs and data. The storage 9 is used also as a work area that temporarily stores a processing result of the controller 10. The storage 9 may include any non-transitory storage medium such as a semiconductor storage medium and a magnetic storage medium. The storage 9 may include a plurality type of storage mediums. The storage 9 may include a combination of a portable storage medium such as a memory card, an optical disc, or a magneto-optical disc with a reader of the storage medium. The storage 9 may include a storage device used as a temporary storage area such as Random Access Memory (RAM).

Programs stored in the storage 9 include applications executed in the foreground or the background and a control program for assisting operations of the applications. The application causes the controller 10, for example, to display a screen on the display 20 and perform a process according to a gesture detected through the touch screen 21. The control program is, for example, an OS. The applications and the control program may be installed in the storage 9 through wireless communication by the communication unit 6 or through a non-transitory storage medium.

The storage 9 stores therein a control program 9A, a phone call application 9C, and setting data 9Z, for example. The phone call application 9C provides a call function for making calls by wireless communication. The setting data 9Z includes information about various settings and various types of processing related to the operation of the mobile phone 1. For example, the setting data 9Z includes olfactory sensor management information for managing whether the olfactory sensor 4c is active or not.

The control program 9A provides functions about various types of control for operating the mobile phone 1. The control program 9A achieves making calls by controlling the communication unit 6, the microphone 8, and the like, for example. The functions provided by the control program 9A may be used by being combined with functions provided by another program such as the phone call application 9C in some cases.

Furthermore, the control program 9A includes a function of activating the olfactory sensor 4c when the phone call function is in execution. When at least a function provided by the phone call application 9C is executed, it is determined that the phone call function is in execution. Examples of the state in which the function provided by the phone call application 9C is executed include a state in which a user interface used to perform an operation for a phone call is displayed on the display 20 in association with an operation of the user. Examples of the state in which the function provided by the phone call application 9C is executed include a state in which an incoming call screen for informing the user of an incoming call is displayed on the display 20. Examples of the state in which the function provided by the phone call application 9C is executed include a state from when processing for a phone call is started through a telephone connection established in association with an outgoing call operation performed by the user on the user interface to when the processing for the phone call is terminated. Examples of the state in which the function provided by the phone call application 9C is executed include a state from when the processing for a phone call is started through a telephone connection established in association with an incoming-call response operation performed by the user on the incoming call screen to when the processing for the phone call is terminated. Examples of the case in which the processing for the phone call is terminated include a case in which a call ending operation is performed by the user, a case in which the telephone connection is released by the call partner (phone conversation is terminated by the call partner), a case in which the telephone connection is disconnected, etc. The execution of the phone call application 9C may be stopped in response to the termination of the processing for the phone call. Alternatively, the execution of the phone call application 9C may be continued even when the processing for the phone call is terminated. In this case, the execution of the phone call application 9C is stopped by an operation for terminating the phone call application 9C such as an end operation (deletion from the display 20, etc.) of the user interface used to perform an operation for a phone call.

The controller 10 is a processing unit. Examples of the processing units include, but are not limited to, a Central Processing Unit (CPU), System-on-a-chip (SoC), a Micro Control Unit (MCU), and a Field-Programmable Gate Array (FPGA). The controller 10 integrally controls the operations of the mobile phone 1 to implement various functions.

Specifically, the controller 10 executes instructions contained in the program stored in the storage 9 while referring to the data stored in the storage 9 as necessary. The controller 10 controls a function unit according to the data and the instructions to thereby implement the various functions. Examples of the function unit include, but are not limited to, the display 20, the communication unit 6, the microphone 8, the speaker 11, and the vibrator 18. The controller 10 can change the control according to the detection result of a detector. Examples of the detectors include, but are not limited to, the buttons 3, the illumination sensor 19, the proximity sensor 5, the olfactory sensor 4c, the camera 12, the attitude detection unit 15, and the touch screen 21.

When the phone call function is in execution, the controller 10 activates the olfactory sensor 4c by executing the control program 9A, for example. When at least the function provided by the phone call application 9C is in execution, the controller 10 determines that the phone call function is in execution. For example, when the user interface used to perform an operation for a phone call is displayed on the display 20, the controller 10 determines that the phone call function is in execution. For example, when the incoming call screen for informing the user of an incoming call is displayed on the display 20, the controller 10 determines that the phone call function is in execution. For example, the controller 10 determines that the phone call function is in execution during a period of time from when the processing for a phone call is started through a telephone connection established in association with an outgoing call operation performed by the user on the user interface to when the processing for the phone call is terminated. For example, the controller 10 determines that the phone call function is in execution during a period of time from when the processing for a phone call is started through a telephone connection established in association with an incoming-call response operation performed by the user on the incoming call screen to when the processing for the phone call is terminated. When the processing for the phone call is terminated, the controller 10 determines that the execution of the phone call application 9C is also stopped. Examples of the case in which the processing for the phone call is terminated include a case in which a call ending operation is performed by the user, a case in which the telephone connection is released by the call partner (phone conversation is terminated by the call partner), a case in which the telephone connection is disconnected, etc. Even when the processing for the phone call is terminated, the controller 10 may determine that the phone call function is in execution until an end operation or the like (deletion from the display 20, etc.) of the user interface used to perform an operation for a phone call is performed.

In the present application, examples of activating a computer program (or application) by the controller 10 include: reading newly the computer program stored in the storage 9 and starting the process thereof; and starting newly the process of a computer program that has already been read. In the present application, examples of executing a computer program by the controller 10 include: activating the computer program; resuming the computer program that is currently suspended; and continuing the process of the computer program that has been activated.

Part or all of the programs and the data stored in the storage 9 in FIG. 21 may be downloaded from any other device through wireless communication by the communication unit 6. Part or all of the programs and the data stored in the storage 9 in FIG. 21 may be stored in the non-transitory storage medium that can be read by the reader included in the storage 9. Examples of the non-transitory storage mediums include, but are not limited to, an optical disc such as CD, DVD, and Blu-ray, a magneto-optical disc, magnetic storage medium, a memory card, and solid-state storage medium.

The speaker 11 is a sound output unit that outputs a sound. The speaker is a dynamic speaker, for example, which transmits a sound converted from an electric signal to a user and so on. The speaker 22 is used to output a voice of a phone call, or a sound of music contents or moving image contents, for example. The speaker 11 is called a receiver in some times when it is used mainly for outputting a voice of a phone call.

The camera 12 is an in-camera for photographing an object facing the display 20. The camera 12 converts a photographed image to electric signals. The mobile phone 1 may include an out-camera for photographing an object facing the other side of the display 20 in addition to the camera 12.

The attitude detection unit 12 detects attitude of the mobile phone 1. The attitude detection unit 12 includes at least one of an acceleration sensor, direction sensor, and gyroscope to detect the attitude.

The vibrator 18 vibrates part or the whole of the mobile phone 1. The vibrator includes a piezoelectric element, an eccentric motor, or the like to generate vibration, for example. The vibration generated by the vibrator 18 is used not to transmit sounds but to notify a user of a various type of events such as an incoming call.

The touch screen 21 detects contact with the touch screen 21. The touch screen is used to detect a contact operation by a user with a finger, a pen, a stylus pen, or the like. Examples of the gesture detected via the touch screen 21 include, but are not limited to, a touch, a long touch, a release, a swipe, a tap, a double-tap, a long tap, a drag, a flick, a pinch-in, and a pinch-out. Any technology such as capacitive sensing, resistive sensing, surface acoustic wave (or ultrasonic) sensing, infrared sensing, electromagnetic induction sensing, and load sensing, may be used to allow the touch screen 21 to detect contact.

The functional configuration of the mobile phone 1 illustrated in FIG. 21 is only an example, and therefore it can be modified as required within a scope that does not depart from the gist of the present invention. For example, the mobile phone 1 may not be provided with the attitude detection unit 15 and the touch screen 21.

Figure 22:
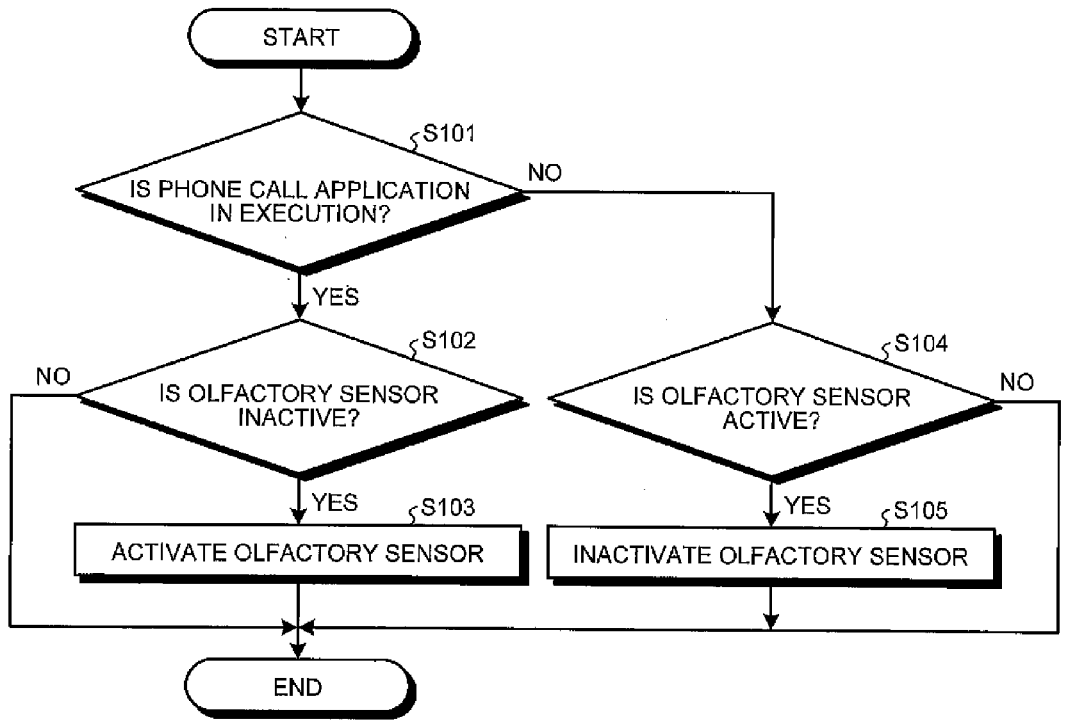
FIG. 22 is a diagram of an example of a processing procedure by the mobile phone according to Embodiment 3.

An example of a processing procedure of the mobile phone 1 according to Embodiment 3 will be explained below with reference to FIG. 22. FIG. 22 is a diagram of an example of the processing procedure by the mobile phone according to Embodiment 3. The processing procedure illustrated in FIG. 22 is implemented by the controller 10 executing the control program 9A and the like stored in the storage 9. The processing procedure illustrated in FIG. 22 is repeatedly performed by the controller 10 while the mobile phone 1 operates.

As illustrated in FIG. 22, at Step S101, the controller 10 determines whether the phone call application 9C is in execution. When the function provided by the phone call application 9C is in execution, the controller 10 determines that the phone call application 9C is in execution. Examples of the case in which the function provided by the phone call application 9C is in execution include a state in which the user interface used to perform an operation for a phone call is displayed on the display 20 in association with a user operation. Furthermore, examples of the state in which the function provided by the phone call application 9C is executed include a state in which the incoming call screen for informing the user of an incoming call is displayed on the display 20. Moreover, examples of the state in which the function provided by the phone call application 9C is executed include a state from when the processing for a phone call is started through a telephone connection established in association with an outgoing call operation performed by the user on the user interface to when the processing for the phone call is terminated. Furthermore, examples of the state in which the function provided by the phone call application 9C is executed include a state from when the processing for a phone call is started through a telephone connection established in association with an incoming-call response operation performed by the user on the incoming call screen to when the processing for the phone call is terminated.

When the phone call application 9C is in execution as a result of determination (Yes at Step S101), then at Step S102, the controller 10 determines whether the olfactory sensor 4c is inactive.

When the olfactory sensor 4c is inactive as a result of determination (Yes at Step S102), then at Step S103, the controller 10 activates the olfactory sensor 4c and ends the processing procedure illustrated in FIG. 22. Meanwhile, when the olfactory sensor 4c is not inactive (i.e. when it is active) as a result of determination (No at Step S102), the controller 10 directly ends the processing procedure illustrated in FIG. 22.

When the phone call application 9C is not in execution as a result of determination at Step S101 (No at Step S101), then at Step S104, the controller 10 determines whether the olfactory sensor 4c is active.

When the olfactory sensor 4c is active as a result of determination (Yes at Step S104), then at Step S105, the controller 10 inactivates the olfactory sensor 4c and ends the processing procedure illustrated in FIG. 22. Meanwhile, when the olfactory sensor 4c is not active (i.e. when it is inactive) as a result of determination (No at Step S104), the controller 10 directly ends the processing procedure illustrated in FIG. 22.

Figure 23:
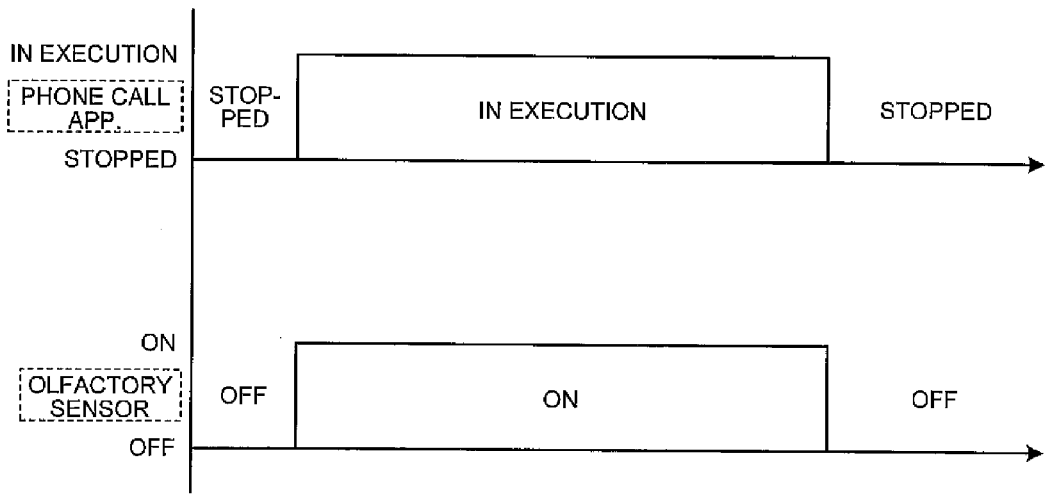
FIG. 23 is a diagram of a relationship between an execution state of a phone call application according to Embodiment 3 and an operation state of an olfactory sensor.

FIG. 23 is a diagram of a relationship between an execution state of the phone call application according to Embodiment 3 and an operation state of the olfactory sensor. According to the processing procedure illustrated in FIG. 22, as illustrated in FIG. 23, when the phone call application 9C activated in response to, for example, a user operation or an incoming call is in execution, the mobile phone 1 operates (activates) the olfactory sensor 4c. Meanwhile, when the phone call application 9C is stopped, the mobile phone 1 does not operate (inactivates) the olfactory sensor 4c. Therefore, according to Embodiment 3, the power consumed by the olfactory sensor 4c when data for the user is measured can be reduced as much as possible. Moreover, according to Embodiment 3, when a target to be measured by the olfactory sensor 4c is, for example, a concentration of the specific substance contained in the breath of the user, measurement data can be effectively acquired.

Embodiment 4

Embodiment 4 will explain an example of activating the olfactory sensor 4c when an outgoing call operation is performed by the user. A functional configuration of a mobile phone according to Embodiment 4 is basically the same as that of Embodiment 3 but some points described below are different.

The control program 9A includes a function of activating the olfactory sensor 4c when the outgoing call operation is performed. Examples of the outgoing call operation include an operation using the button 3. Examples of the outgoing call operation include an operation performed by the user to make an outgoing call on the user interface used to perform an operation for a phone call. The operation performed by the user on the user interface used to perform an operation for a phone call is determined based on the detection result of the touch screen 21.

The controller 10 activates the olfactory sensor 4c by executing, for example, the control program 9A when the outgoing call operation is performed.

Figure 24:
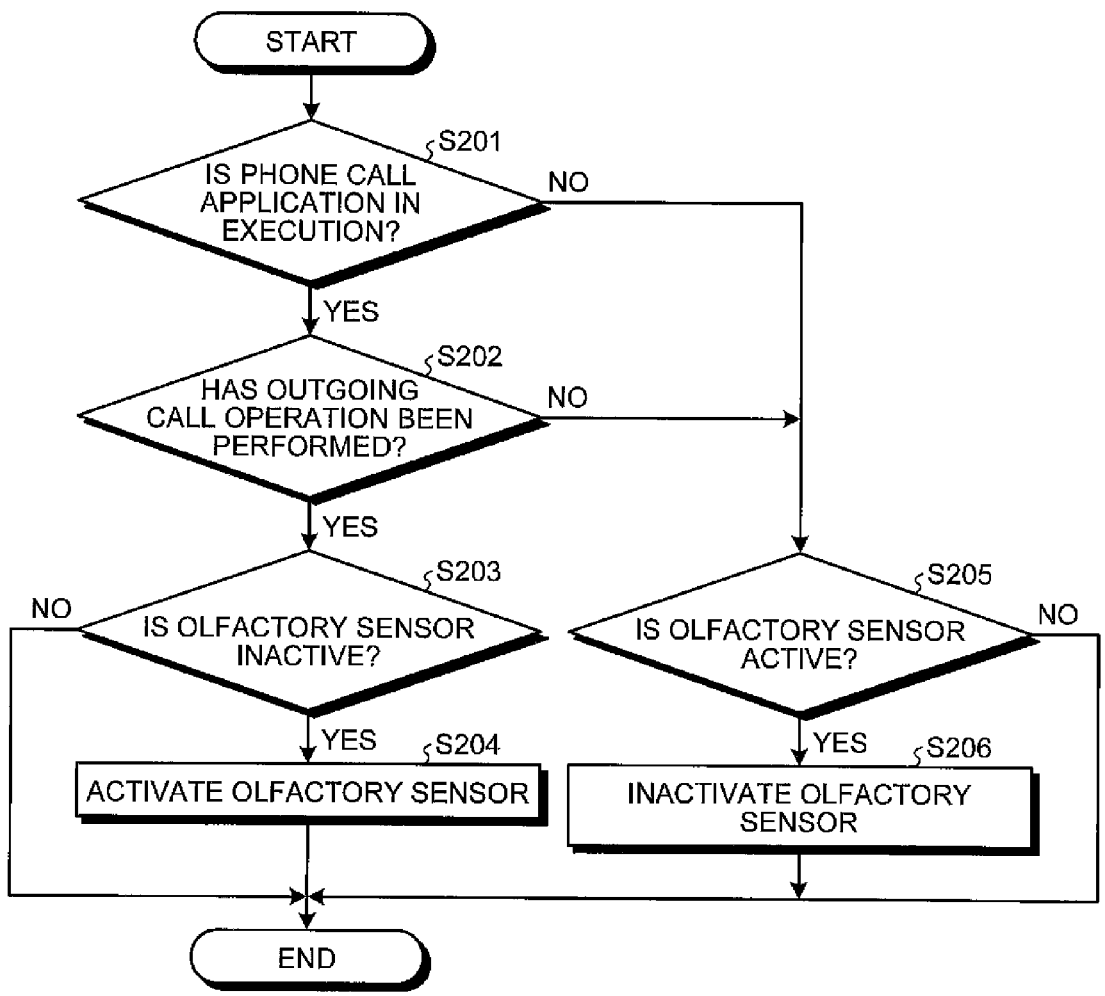
FIG. 24 is a diagram of an example of a processing procedure by a mobile phone according to Embodiment 4.

An example of a processing procedure of the mobile phone 1 according to Embodiment 4 will be explained below with reference to FIG. 24. FIG. 24 is a diagram of an example of the processing procedure by the mobile phone according to Embodiment 4. The processing procedure illustrated in FIG. 24 is implemented by the controller 10 executing the control program 9A or the like stored in the storage 9. The processing procedure illustrated in FIG. 24 is repeatedly performed by the controller 10 while the mobile phone 1 operates.

As illustrated in FIG. 24, at Step S201, the controller 10 determines whether the phone call application 9C is in execution.

When the phone call application 9C is in execution as a result of determination (Yes at Step S201), then at Step S202, the controller 10 determines whether the outgoing call operation has been performed. When the outgoing call operation has been performed as a result of determination (Yes at Step S202), then at Step S203, the controller 10 determines whether the olfactory sensor 4c is inactive.

When the olfactory sensor 4c is inactive as a result of determination (Yes at Step S203), then at Step S204, the controller 10 activates the olfactory sensor 4c and ends the processing procedure illustrated in FIG. 24. Meanwhile, when the olfactory sensor 4c is not inactive (i.e. when it is active) as a result of determination (No at Step S203), the controller 10 directly ends the processing procedure illustrated in FIG. 24.

When the outgoing call operation is not performed as a result of determination at Step S202 (No at Step S202), then at Step S205, the controller 10 determines whether the olfactory sensor 4c is active.

When the olfactory sensor 4c is active as a result of determination (Yes at Step S205), then at Step S206, the controller 10 inactivates the olfactory sensor 4c and ends the processing procedure illustrated in FIG. 24. Meanwhile, when the olfactory sensor 4c is not active (i.e. when it is inactive) as a result of determination (No at Step S205), the controller 10 directly ends the processing procedure illustrated in FIG. 24.

When the phone call application 9C is not in execution as a result of determination at Step S201 (No at Step S201), then the controller 10 proceeds to Step S205, and determines whether the olfactory sensor 4c is active.

Figure 25:
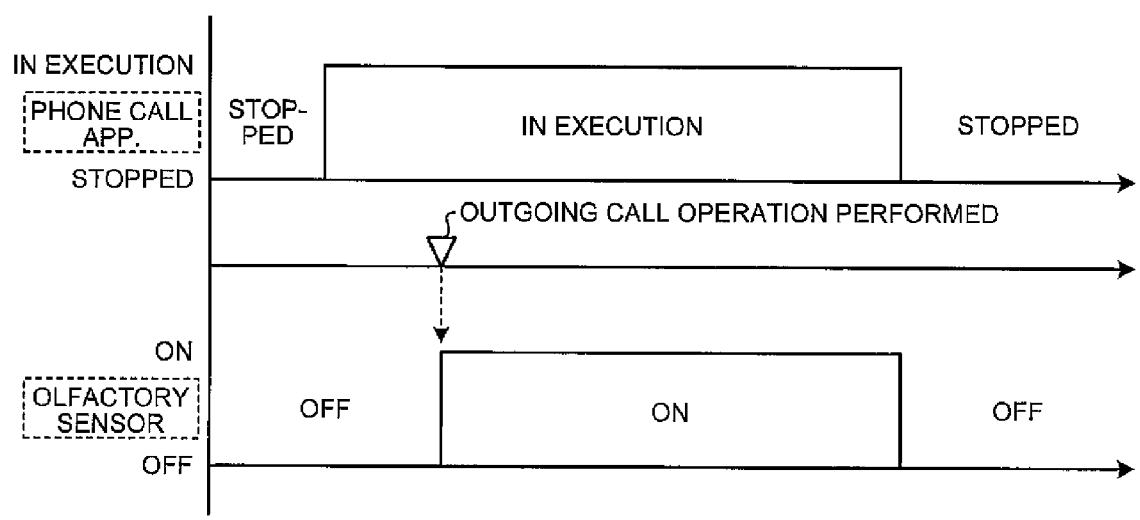
FIG. 25 is a diagram of a relationship between an execution state of a phone call application according to Embodiment 4 and an operation state of an olfactory sensor.

FIG. 25 is a diagram of a relationship between an execution state of the phone call application according to Embodiment 4 and an operation state of the olfactory sensor. According to the processing procedure illustrated in FIG. 24, as illustrated in FIG. 25, when the phone call application 9C activated in response to a user operation is in execution, the mobile phone 1 starts the operation of the olfactory sensor 4c at a timing when the outgoing call operation is performed by the user. The mobile phone 1 does not start the operation of the olfactory sensor 4c even during the execution of the phone call application 9C if the user does not perform an outgoing call operation. Therefore, according to Embodiment 4, the power consumed by the olfactory sensor 4c when the data for the user is measured can be reduced more than that of the example illustrated in Embodiment 3. Moreover, according to Embodiment 4, when a target to be measured by the olfactory sensor 4c is, for example, a concentration of the specific substance contained in the breath of the user, measurement data can be more effectively acquired than that of the example illustrated in Embodiment 3. It is easily assumed that a speech utterance is provided by the user when the outgoing call operation is performed by the user. Based on this assumption, it is considered that, in many cases, the speech utterance is not provided by the user until a phone call is started. Therefore, a case where the operation is started at a timing of the outgoing call operation can reduce a wasteful operation time during which measurement data cannot be obtained, of the operation time of the olfactory sensor 4c, more than that of the case where the olfactory sensor 4c is operated during the execution of the phone call application 9C. Thus, the measurement data can be effectively acquired.

Embodiment 5

Embodiment 5 will explain an example of activating the olfactory sensor 4c when a telephone connection is established in response to an outgoing call operation performed by the user. A functional configuration of a mobile phone according to Embodiment 5 is basically the same as that of Embodiment 3 but some points described below are different.

The control program 9A includes a function of activating the olfactory sensor 4c when a telephone connection is established in response to an outgoing call operation performed by the user.

The controller 10 activates the olfactory sensor 4c by executing, for example, the control program 9A when the telephone connection is established in response to the outgoing call operation performed by the user.

Figure 26:
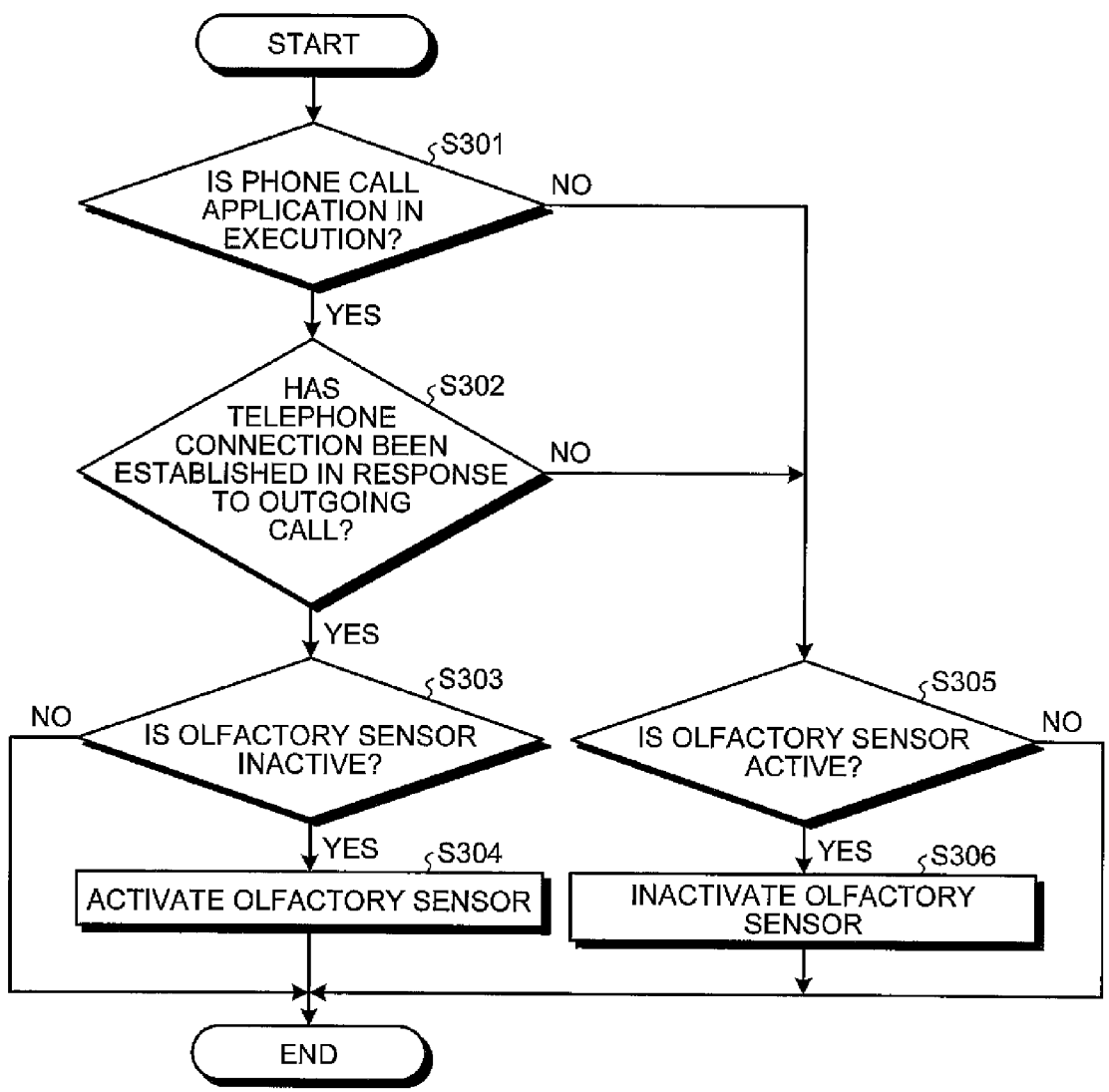
FIG. 26 is a diagram of an example of a processing procedure by a mobile phone according to Embodiment 5.

An example of a processing procedure of the mobile phone 1 according to Embodiment 5 will be explained below with reference to FIG. 26. FIG. 26 is a diagram of an example of the processing procedure by the mobile phone 1 according to Embodiment 5. The processing procedure illustrated in FIG. 26 is implemented by the controller 10 executing the control program 9A or the like stored in the storage 9. The processing procedure illustrated in FIG. 26 is repeatedly performed by the controller 10 while the mobile phone 1 operates.

As illustrated in FIG. 26, at Step S301, the controller 10 determines whether the phone call application 9C is in execution.

When the phone call application 9C is in execution as a result of determination (Yes at Step S301), then at Step S302, the controller 10 determines whether a telephone connection has been established in response to the outgoing call operation. When the telephone connection has been established in response to the outgoing call operation as a result of determination (Yes at Step S302), then at Step S303, the controller 10 determines whether the olfactory sensor 4c is inactive.

When the olfactory sensor 4c is inactive as a result of determination (Yes at Step S303), then at Step S304, the controller 10 activates the olfactory sensor 4c and ends the processing procedure illustrated in FIG. 26. Meanwhile, when the olfactory sensor 4c is not inactive (i.e. when it is active) as a result of determination (No at Step S303), the controller 10 directly ends the processing procedure illustrated in FIG. 26.

When the telephone connection has not been established in response to the outgoing call operation as a result of determination at Step S302 (No at Step S302), then at Step S305, the controller 10 determines whether the olfactory sensor 4c is active.

When the olfactory sensor 4c is active as a result of determination (Yes at Step S305), then at Step S306, the controller 10 inactivates the olfactory sensor 4c and ends the processing procedure illustrated in FIG. 26. Meanwhile, when the olfactory sensor 4c is not active (i.e. when it is inactive) as a result of determination (No at Step S305), the controller 10 directly ends the processing procedure illustrated in FIG. 26.

When the phone call application 9C is not in execution as a result of determination at Step S301 (No at Step S301), then the controller 10 proceeds to Step S305, and determines whether the olfactory sensor 4c is active.

Figure 27:
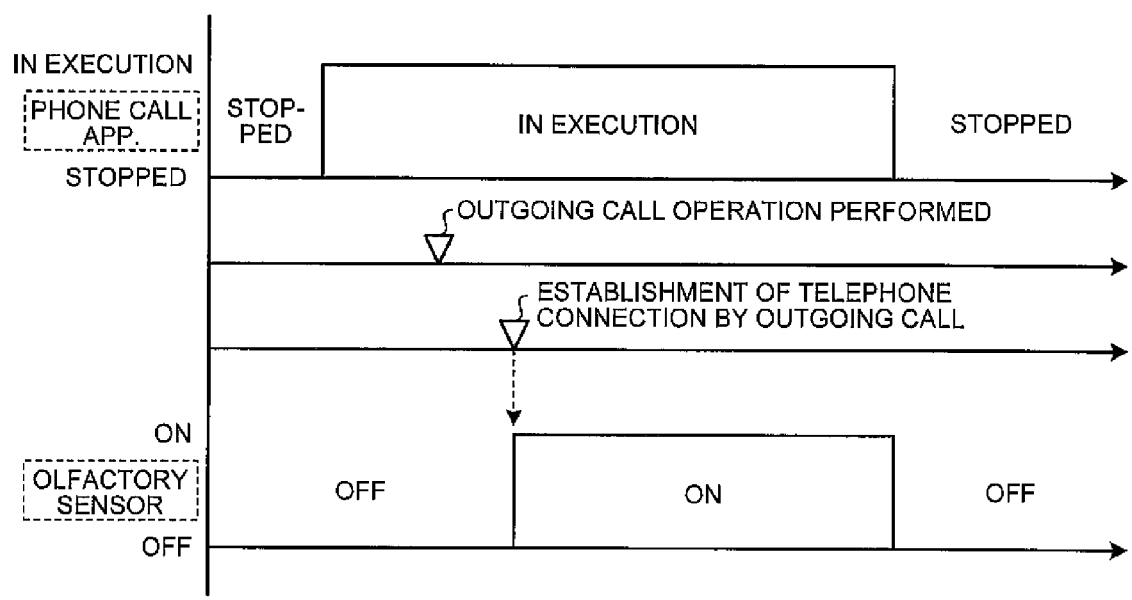
FIG. 27 is a diagram of a relationship between an execution state of a phone call application according to Embodiment 5 and an operation state of an olfactory sensor.

FIG. 27 is a diagram of a relationship between an execution state of the phone call application according to Embodiment 5 and an operation state of the olfactory sensor. According to the processing procedure illustrated in FIG. 26, as illustrated in FIG. 27, when the phone call application 9C activated in response to a user operation is in execution, the mobile phone 1 starts the operation of the olfactory sensor 4c at a timing when a telephone connection is established in response to the outgoing call operation performed by the user. The mobile phone 1 does not start the operation of the olfactory sensor 4c even during the execution of the phone call application 9C if the telephone connection is not established in response to the outgoing call operation performed by the user. Therefore, according to Embodiment 5, the power consumed by the olfactory sensor 4c when the data for the user is measured can be further reduced than that of the example illustrated in Embodiment 4. Moreover, according to Embodiment 5, when a target to be measured by the olfactory sensor 4c is, for example, a concentration of the specific substance contained in the breath of the user, measurement data can be more effectively acquired than that of the example illustrated in Embodiment 4. It is assumed that a speech utterance is often started from the user side when a telephone connection is established in response to the outgoing call operation. Based on this assumption, it is considered that, in many cases, the speech utterance is not provided by the user until the telephone connection is established. Therefore, a case where the operation is started at a timing of the establishment of the telephone connection can reduce the wasteful operation time more than that of the case where the olfactory sensor 4c is operated at the timing of the outgoing call operation. Thus, the measurement data can be effectively acquired.

Embodiment 6

Embodiment 6 will explain an example of activating the olfactory sensor 4c when a sound pressure level of a sound input to the microphone 8 reaches a certain value or higher after the establishment of the telephone connection in response to the outgoing call operation performed by the user. A functional configuration of a mobile phone according to Embodiment 6 is basically the same as that of Embodiment 3 but some points described below are different.

The setting data 9Z includes the certain value used to determine that a sound (sound signal) input to the microphone 8 is a voice input by the speech utterance of the user.

The control program 9A includes a function of activating the olfactory sensor 4c when the sound pressure level of a sound input to the microphone 8 reaches the certain value or higher after the establishment of the telephone connection in response to the outgoing call operation performed by the user.

The controller 10 activates the olfactory sensor 4c by executing, for example, the control program 9A, when the sound pressure level of a sound input to the microphone 8 reaches the certain value or higher after the establishment of the telephone connection in response to the outgoing call operation performed by the user.

Figure 28:
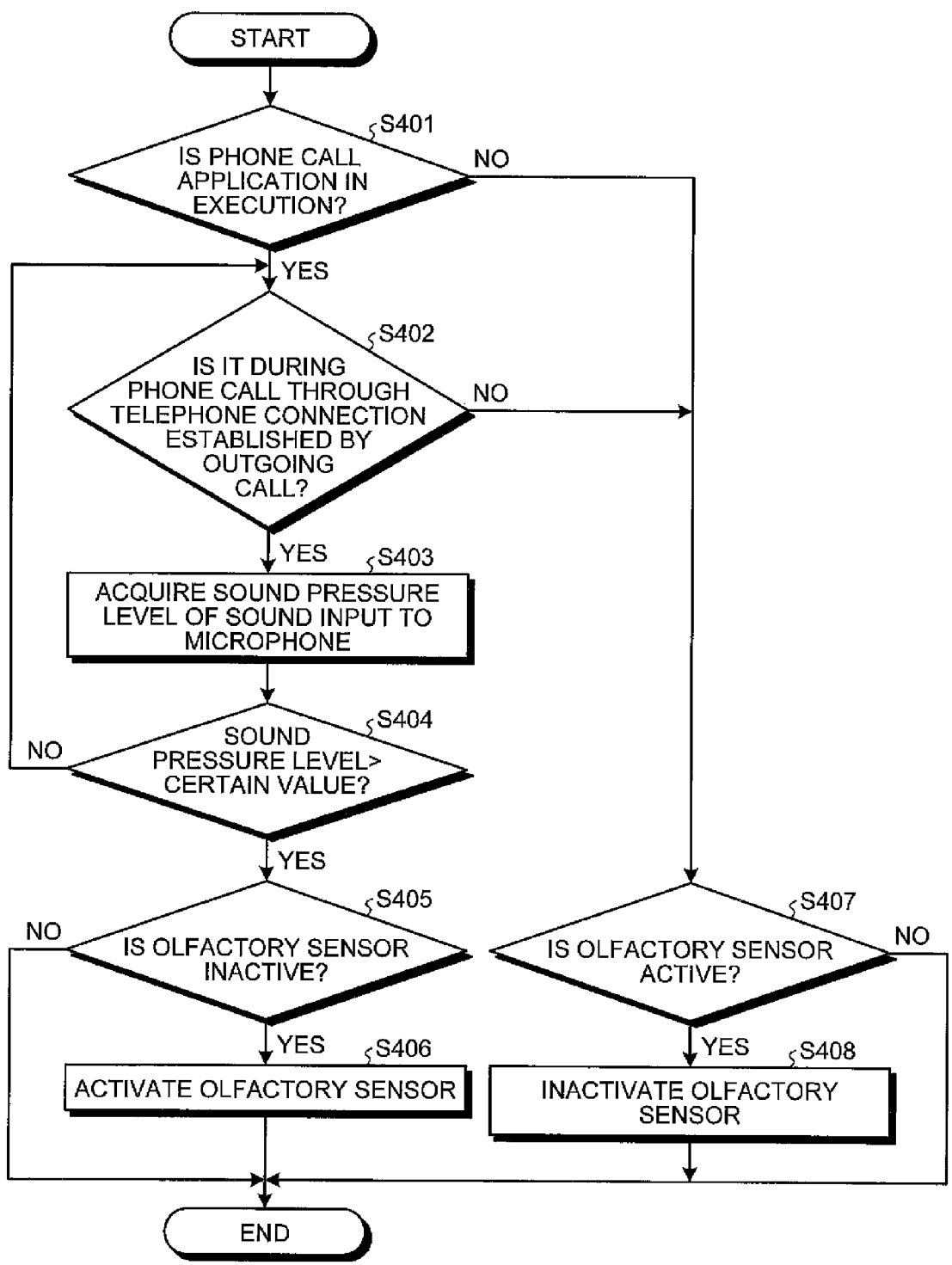
FIG. 28 is a diagram of an example of a processing procedure by a mobile phone according to Embodiment 6.

An example of a processing procedure of the mobile phone 1 according to Embodiment 6 will be explained below with reference to FIG. 28. FIG. 28 is a diagram of an example of the processing procedure by the mobile phone according to Embodiment 6. The processing procedure illustrated in FIG. 28 is implemented by the controller 10 executing the control program 9A or the like stored in the storage 9. The processing procedure illustrated in FIG. 28 is repeatedly performed by the controller 10 while the mobile phone 1 operates.

As illustrated in FIG. 28, at Step S401, the controller 10 determines whether the phone call application 9C is in execution.

When the phone call application 9C is in execution as a result of determination (Yes at Step S401), then at Step S402, the controller 10 determines whether it is during a phone call through the telephone connection established by the outgoing call. When it is during a phone call through the telephone connection established by the outgoing call as a result of determination (Yes at Step S402), then at Step S403, the controller 10 acquires the sound pressure level of the sound (sound signal) input to the microphone 8.

Subsequently, at Step S404, the controller 10 determines whether the sound pressure level of the sound (sound signal) input to the microphone 8 is the certain value or higher. When the sound pressure level of the sound (sound signal) input to the microphone 8 is not the certain value or higher as a result of determination (No at Step S404), the controller 10 returns to the processing procedure at Step S402, i.e., to the determination as to whether it is during a phone call through the telephone connection established by the outgoing call. Meanwhile, when the sound pressure level of the sound (sound signal) input to the microphone 8 is the certain value or higher as a result of determination (Yes at Step S404), then at Step S405, the controller 10 determines whether the olfactory sensor 4c is inactive.

When the olfactory sensor 4c is inactive as a result of determination (Yes at Step S405), then at Step S406, the controller 10 activates the olfactory sensor 4c and ends the processing procedure illustrated in FIG. 28. Meanwhile, when the olfactory sensor 4c is not inactive (i.e. when it is active) as a result of determination (No at Step S405), the controller 10 directly ends the processing procedure illustrated in FIG. 28.

When it is not during a phone call through the telephone connection established by the outgoing call as a result of determination at Step S402 (No at Step S402), then at Step S407, the controller 10 determines whether the olfactory sensor 4c is active.

When the olfactory sensor 4c is active as a result of determination (Yes at Step S407), then at Step S408, the controller 10 inactivates the olfactory sensor 4c and ends the processing procedure illustrated in FIG. 28. Meanwhile, when the olfactory sensor 4c is not active (i.e. when it is inactive) as a result of determination (No at Step S407), the controller 10 directly ends the processing procedure illustrated in FIG. 28.

When the phone call application 9C is not in execution as a result of determination at Step S401 (No at Step S401), then the controller 10 proceeds to Step S407, and determines whether the olfactory sensor 4c is active.

Figure 29:
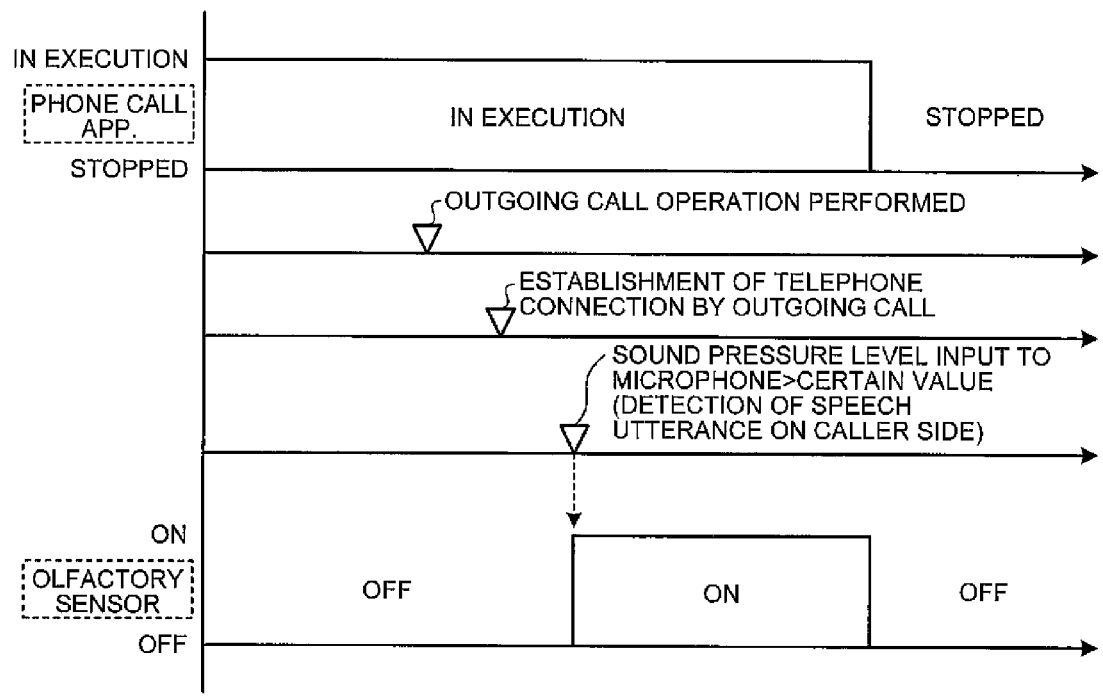
FIG. 29 is a diagram of a relationship between an execution state of a phone call application according to Embodiment 6 and an operation state of an olfactory sensor.

FIG. 29 is a diagram of a relationship between an execution state of the phone call application according to Embodiment 6 and an operation state of the olfactory sensor. According to the processing procedure illustrated in FIG. 28, as illustrated in FIG. 29, when the phone call application 9C activated in response to the user operation is in execution, the mobile phone 1 starts the operation of the olfactory sensor 4c at a timing when the sound pressure of the sound input to the microphone 8 reaches the certain value or higher after the phone call is started through the telephone connection established in response to the outgoing call operation performed by the user. In other words, the mobile phone 1 starts the operation of the olfactory sensor 4c at a timing when the speech utterance of the user is detected after the phone call is started.

The mobile phone 1 does not start the operation of the olfactory sensor 4c even after the phone call is started through the telephone connection established in response to the outgoing call operation if the sound pressure of the sound input to the microphone 8 does not reach the certain value or higher. Therefore, according to Embodiment 6, the power consumed by the olfactory sensor 4c when the data for the user is measured can be further reduced than that of the example illustrated in Embodiment 5. Moreover, according to Embodiment 6, when a target to be measured by the olfactory sensor 4c is, for example, a concentration of the specific substance contained in the breath of the user, measurement data can be more effectively acquired than that of the example illustrated in Embodiment 5. In other words, the case where the operation of the olfactory sensor 4c is started at a timing of the speech utterance of the user can further reduce the wasteful operation time during which the measurement data cannot be obtained, of the operation time of the olfactory sensor 4c, than that of the case where the operation of the olfactory sensor 4c is started at a timing of the establishment of the telephone connection. Thus, the measurement data can be effectively acquired.

Embodiment 7

Embodiment 4 to Embodiment 6 have explained the examples of the processing performed when an outgoing call is performed by the user of the mobile phone 1. In the following, Embodiment 7 will explain an example of processing performed when the mobile phone 1 receives an incoming call. A functional configuration of a mobile phone according to Embodiment 7 is basically the same as that of Embodiment 3 but some points described below are different.

The control program 9A includes a function of activating the olfactory sensor 4c when an incoming-call response operation is performed. Examples of the incoming-call response operation include an operation using, for example, the button 3. Examples of the incoming-call response operation include an operation performed by the user to respond to an incoming call on the user interface used to perform an operation for a phone call. The operation performed by the user on the user interface used to perform an operation for a phone call is determined based on the detection result of the touch screen 21.

The controller 10 activates the olfactory sensor 4c by executing, for example, the control program 9A when the incoming-call response operation is performed.

Figure 30:
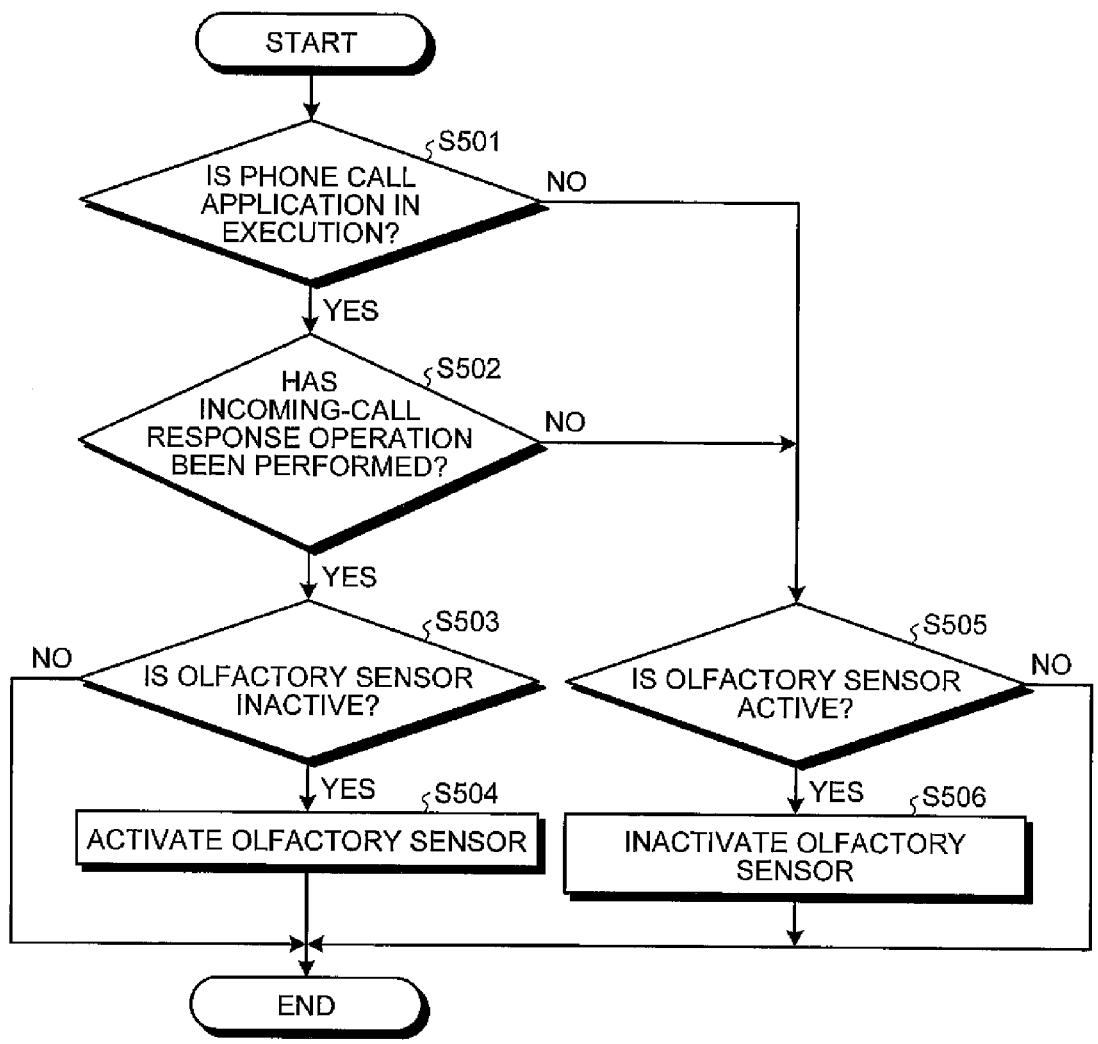
FIG. 30 is a diagram of an example of a processing procedure by a mobile phone according to Embodiment 7.

An example of a processing procedure of the mobile phone 1 according to Embodiment 7 will be explained below with reference to FIG. 30. FIG. 30 is a diagram of an example of the processing procedure by the mobile phone according to Embodiment 7. The processing procedure illustrated in FIG. 30 is implemented by the controller 10 executing the control program 9A or the like stored in the storage 9. The processing procedure illustrated in FIG. 30 is repeatedly performed by the controller 10 while the mobile phone 1 operates.

As illustrated in FIG. 30, at Step S501, the controller 10 determines whether the phone call application 9C is in execution.

When the phone call application 9C is in execution as a result of determination (Yes at Step S501), then at Step S502, the controller 10 determines whether an incoming-call response operation has been performed. When the incoming-call response operation has been performed as a result of determination (Yes at Step S502), then at Step S503, the controller 10 determines whether the olfactory sensor 4c is inactive.

When the olfactory sensor 4c is inactive as a result of determination (Yes at Step S503), then at Step S504, the controller 10 activates the olfactory sensor 4c and ends the processing procedure illustrated in FIG. 30. Meanwhile, when the olfactory sensor 4c is not inactive (i.e. when it is active) as a result of determination (No at Step S503), the controller 10 directly ends the processing procedure illustrated in FIG. 30.

When the incoming-call response operation has not been performed as a result of determination at Step S502 (No at Step S502), then at Step S505, the controller 10 determines whether the olfactory sensor 4c is active.

When the olfactory sensor 4c is active as a result of determination (Yes at Step S505), then at Step S506, the controller 10 inactivates the olfactory sensor 4c and ends the processing procedure illustrated in FIG. 30. Meanwhile, when the olfactory sensor 4c is not active (i.e. when it is inactive) as a result of determination (No at Step S505), the controller 10 directly ends the processing procedure illustrated in FIG. 30.

When the phone call application 9C is not in execution as a result of determination at Step S501 (No at Step S501), then the controller 10 proceeds to Step S505, and determines whether the olfactory sensor 4c is active.

Figure 31:
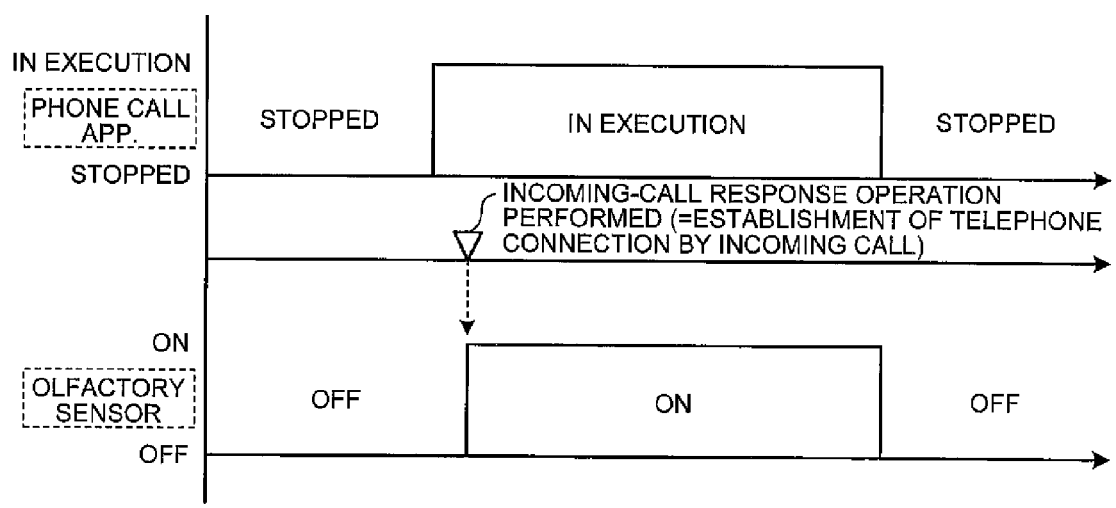
FIG. 31 is a diagram of a relationship between an execution state of a phone call application according to Embodiment 7 and an operation state of an olfactory sensor.

FIG. 31 is a diagram of a relationship between an execution state of the phone call application according to Embodiment 7 and an operation state of the olfactory sensor. According to the processing procedure illustrated in FIG. 30, as illustrated in FIG. 31, the mobile phone 1 starts the operation of the olfactory sensor 4c at a timing when an incoming-call response operation is performed by the user, for example, during the execution of the phone call application 9C activated in response to the incoming call. The mobile phone 1 does not start the operation of the olfactory sensor 4c even during the execution of the phone call application 9C if the incoming-call response operation is not performed by the user. Therefore, according to Embodiment 7, the power consumed by the olfactory sensor 4c when the data for the user is measured can be reduced. Moreover, according to Embodiment 7, when a target to be measured by the olfactory sensor 4c is, for example, a concentration of the specific substance contained in the breath of the user, measurement data can be effectively acquired. In other words, the case where the operation is started at a timing of the incoming-call response operation can reduce the wasteful operation time during which the measurement data cannot be obtained, of the operation time of the olfactory sensor 4c, more than that of the case where the olfactory sensor 4c is operated during the execution of the phone call application 9C. Thus, the measurement data can be effectively acquired.

Embodiment 8

Embodiment 8 will explain an example of activating the olfactory sensor 4c when a sound pressure level of a sound to be output from the speaker 11 reaches a certain value or higher after the establishment of the telephone connection in response to the incoming-call response operation performed by the user. A functional configuration of a mobile phone according to Embodiment 8 is basically the same as that of Embodiment 3 but some points described below are different.

The setting data 9Z includes the certain value used to determine that a sound (sound signal) to be output from the speaker 11 is a voice output by the speech utterance of the call partner.

The control program 9A includes a function of activating the olfactory sensor 4c when the sound pressure level of a sound to be output from the speaker 11 reaches the certain value or higher after the establishment of the telephone connection in response to an incoming-call response operation performed by the user.

The controller 10 activates the olfactory sensor 4c by executing, for example, the control program 9A, when the sound pressure level of a sound to be output from the speaker 11 reaches the certain value or higher after the establishment of the telephone connection in response to the incoming-call response operation performed by the user.

Figure 32:
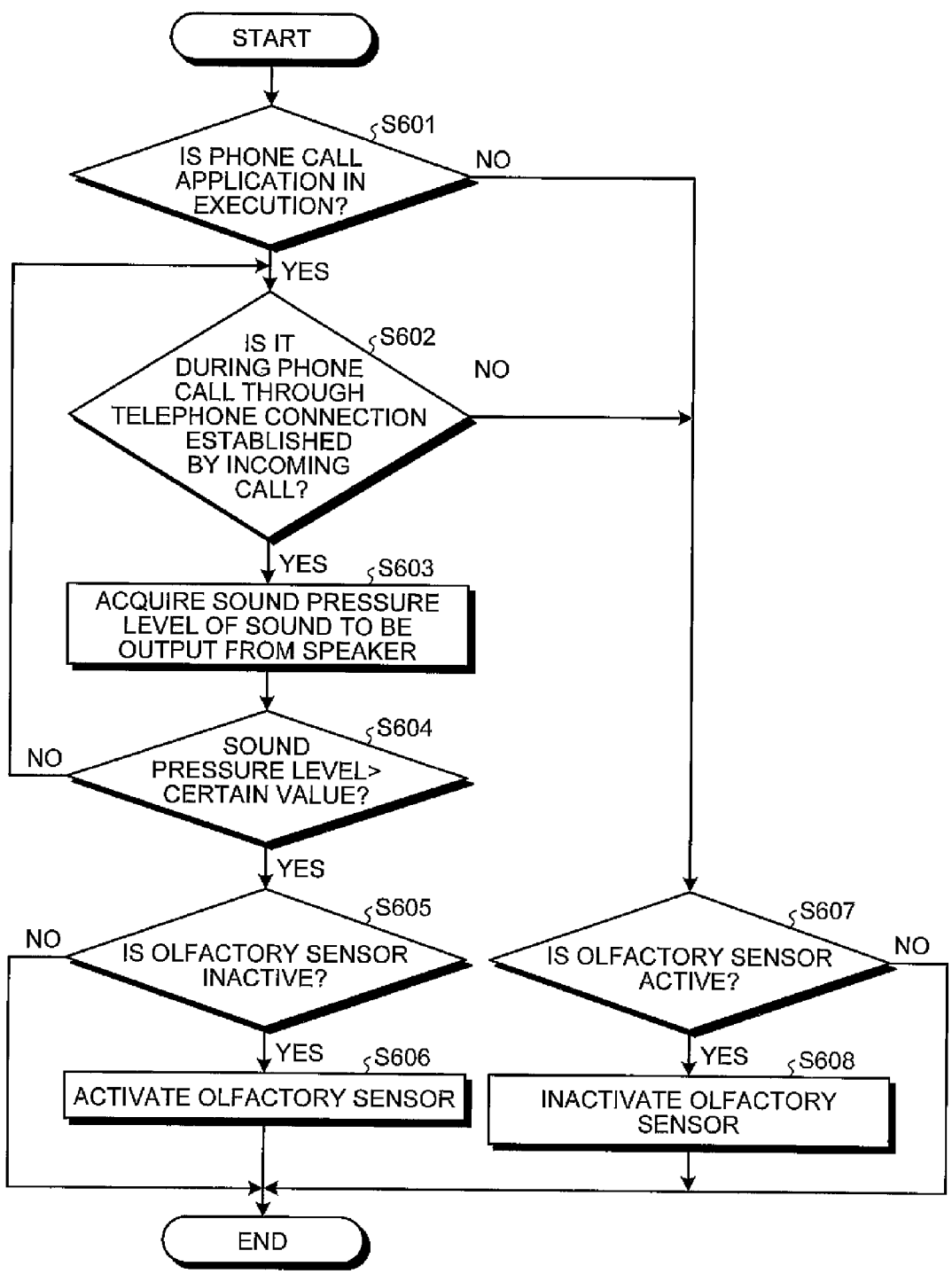
FIG. 32 is a diagram of an example of a processing procedure by a mobile phone according to Embodiment 8.

An example of a processing procedure of the mobile phone 1 according to Embodiment 8 will be explained below with reference to FIG. 32. FIG. 32 is a diagram of an example of the processing procedure by the mobile phone according to Embodiment 8. The processing procedure illustrated in FIG. 32 is implemented by the controller 10 executing the control program 9A or the like stored in the storage 9. The processing procedure illustrated in FIG. 32 is repeatedly performed by the controller 10 while the mobile phone 1 operates.

As illustrated in FIG. 32, at Step S601, the controller 10 determines whether the phone call application 9C is in execution.

When the phone call application 9C is in execution as a result of determination (Yes at Step S601), then at Step S602, the controller 10 determines whether it is during a phone call through the telephone connection established by the incoming call. When it is during a phone call through the telephone connection established by the incoming call as a result of determination (Yes at Step S602), then at Step S603, the controller 10 acquires the sound pressure level of the sound (sound signal) to be output from the speaker 11.

Subsequently, at Step S604, the controller 10 determines whether the sound pressure level of the sound (sound signal) to be output from the speaker 11 is the certain value or higher. When the sound pressure level of the sound (sound signal) to be output from the speaker 11 is not the certain value or higher as a result of determination (No at Step S604), the controller 10 returns to the processing procedure at Step S602, i.e., to the determination as to whether it is during a phone call through the telephone connection established by the incoming call. Meanwhile, when the sound pressure level of the sound (sound signal) to be output from the speaker 11 is the certain value or higher as a result of determination (Yes at Step S604), then at Step S605, the controller 10 determines whether the olfactory sensor 4c is inactive.

When the olfactory sensor 4c is inactive as a result of determination (Yes at Step S605), then at Step S506, the controller 10 activates the olfactory sensor 4c and ends the processing procedure illustrated in FIG. 32. Meanwhile, when the olfactory sensor 4c is not inactive (i.e. when it is active) as a result of determination (No at Step S605), the controller 10 directly ends the processing procedure illustrated in FIG. 32.

When it is not during a phone call through the telephone connection established by the incoming call as a result of determination at Step S602 (No at Step S602), then at Step S607, the controller 10 determines whether the olfactory sensor 4c is active.

When the olfactory sensor 4c is active as a result of determination (Yes at Step S607), then at Step S608, the controller 10 inactivates the olfactory sensor 4c and ends the processing procedure illustrated in FIG. 32. Meanwhile, when the olfactory sensor 4c is not active (i.e. when it is inactive) as a result of determination (No at Step S607), the controller 10 directly ends the processing procedure illustrated in FIG. 32.

When the phone call application 9C is not in execution as a result of determination at Step S601 (No at Step S601), then the controller 10 proceeds to Step S607, and determines whether the olfactory sensor 4c is active.

Figure 33:
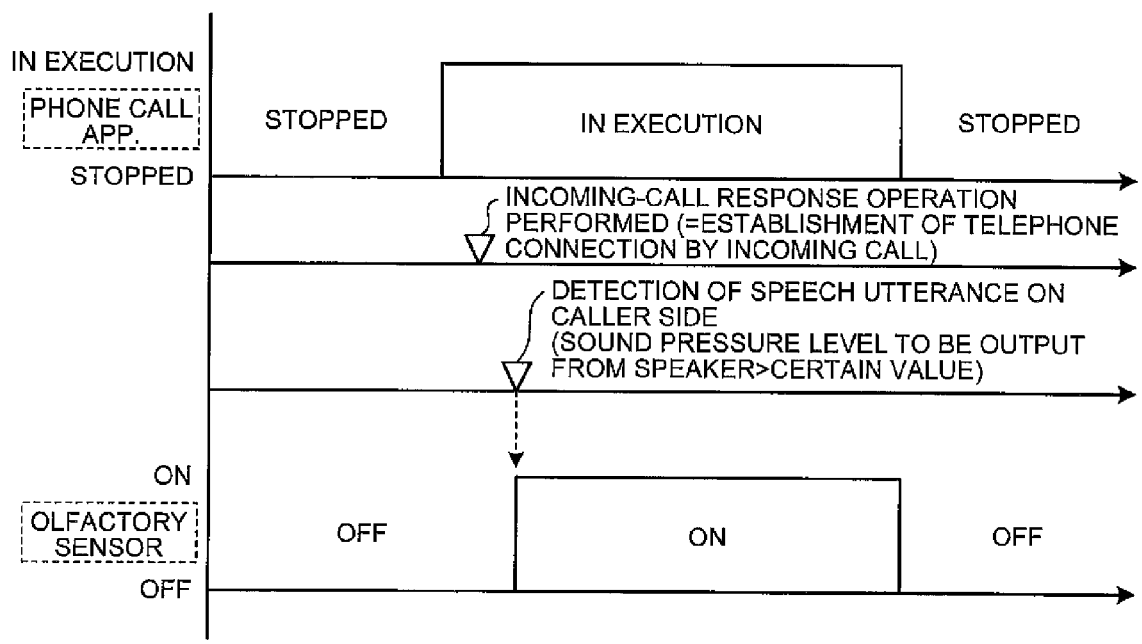
FIG. 33 is a diagram of a relationship between an execution state of a phone call application according to Embodiment 8 and an operation state of an olfactory sensor.

FIG. 33 is a diagram of a relationship between an execution state of the phone call application according to Embodiment 8 and an operation state of the olfactory sensor. According to the processing procedure illustrated in FIG. 32, as illustrated in FIG. 33, the mobile phone 1 starts the operation of the olfactory sensor 4c at a timing when the sound pressure of the sound to be output from the speaker 11 reaches the certain value or higher after the phone call is started through the telephone connection established in response to the incoming-call response operation. In other words, the mobile phone 1 starts the operation of the olfactory sensor 4c at a timing when the speech utterance of the call partner is detected after the phone call is started. The mobile phone 1 does not start the operation of the olfactory sensor 4c even after the phone call is started through the telephone connection established in response to the incoming-call response operation if the sound pressure of the sound to be output from the speaker 11 does not reach the certain value or higher. Therefore, according to Embodiment 8, the power consumed by the olfactory sensor 4c when the data for the user is measured can be further reduced than that of the example illustrated in Embodiment 7. Moreover, according to Embodiment 8, when a target to be measured by the olfactory sensor 4c is, for example, a concentration of the specific substance contained in the breath of the user, measurement data can be more effectively acquired than that of the example illustrated in Embodiment 7. It is assumed that a speech utterance is often started from the call partner when the incoming-call response operation is performed by the user. Based on this assumption, it is considered that, in many cases, the speech utterance by the user is provided after the start of the speech utterance by the call partner. Therefore, the case where the operation of the olfactory sensor 4c is started at a timing of the detection of the speech utterance of the call partner can further reduce the wasteful operation time during which the measurement data cannot be obtained, of the operation time of the olfactory sensor 4c, than that of the case where the operation of the olfactory sensor 4c is started at a timing of the incoming-call response operation. Thus, the measurement data can be effectively acquired. Moreover, in Embodiment 8, the mobile phone 1 may operate the olfactory sensor 4c at a timing of the speech utterance of the user after the incoming call as explained in Embodiment 6, for example.

The embodiments have explained a slate type (straight type) mobile phone as an example of the device according to the appended claims; however, the device according to the appended claims is not limited thereto. The device according to the appended claims may be some other types of mobile phone such as a foldable type and a slidable type. The device according to the appended claims may be any electronic device with a sound input unit other than the mobile phone. Examples of the electronic device with a sound input unit include, but are not limited to, a head set, a tablet, a mobile personal computer, a digital camera, a media player, an electronic book reader, a navigator, a medical equipment, and a gaming device.

Although the art of appended claims has been described with respect to specific embodiments for a complete and clear disclosure, the appended claims are not to be thus limited but are to be construed as embodying all modifications and alternative constructions that may occur to one skilled in the art which fairly fall within the basic teaching herein set forth.

In the embodiments, a predetermined face of the electronic device may be any of the faces 41 to 46 of the housing 40, or may be a face (front side, back side) of the substrate stored inside the housing 40.

The invention claimed is:

1. An electronic device for a phone call, the electronic device comprising: a sound input unit configured to receive a sound during a phone call; a first sensor provided near the sound input unit and configured to detect a substance contained in a first gas; and a second sensor configured to detect the substance contained in a second gas, and a controller configured to remove an influence of the substance contained in the second gas from a detection result of the first sensor based on a detection result of the second sensor, wherein the second sensor is provided on a face, of predetermined faces of the electronic device, different from a face where the first sensor is provided.

2. The electronic device according to claim 1, further comprising a housing provided with an opening configured to capture the sound during the phone call, wherein the sound input unit and at least one of the first and second sensors are provided at positions opposite to the opening of the housing.

3. The electronic device according to claim 2, wherein the first sensor is configured to detect the substance contained in the first gas introduced from the opening.

4. The electronic device according to claim 2, wherein the first sensor is provided in the opening adjacent to the sound input unit.

5. The electronic device according to claim 1, wherein the first sensor is provided on a side where the sound input unit is provided.

6. The electronic device according to cairn 5, wherein at least one of the first and second the sensors is provided at an end of the electronic device.

7. The electronic device according to claim 1, wherein the first sensor is provided to the face adjacent to a face where the sound input unit is provided.

8. The electronic device according to claim 1, wherein the first sensor is formed as a component integrated with the sound input unit.

9. The electronic device according to claim 1, wherein the second sensor is configured to detect the substance contained in the second gas around the electronic device.

10. The electronic device according to claim 1, wherein the first gas in which the substance is detected by the first sensor is a first gas in which the breath of the user of the electronic device and the gas around the electronic device are nixed.

11. An electronic device for a phone call, the electronic device comprising: a first sensor configured to detect a substance contained in a first gas; a sound input unit configured to receive a sound from a user during a phone call; and a controller configured to activate the first sensor when a phone call function is in execution, wherein when a phone call in response to an outgoing call is started by the phone call function, the controller is configured to activate the first sensor when a sound pressure of the sound received at the sound input unit reaches a certain value or higher after establishment of a telephone connection corresponding to the outgoing call.

12. The electronic device according to claim 11, wherein, when a phone call in response to an outgoing call is started by the phone call function, the controller is configured to activate the first sensor when an outgoing call operation for performing the outgoing call is received from the user.

13. The electronic device according to claim 11, wherein, when a phone call in response to an outgoing call is started by the phone call function, the controller is configured to activate the first sensor when a telephone connection corresponding to the outgoing call is established.

14. The electronic device according to claim 11, wherein, when a phone call in response to an incoming call is started by the phone call function, the controller is configured to activate the first sensor when a response operation to respond to the incoming call is received from the user.

15. The electronic device according to claim 11, further comprising a sound output unit configured to output a sound received from a call partner side during the phone call, wherein, when a phone call in response to an incoming call is started by the phone call function, the controller is configured to activate the first sensor when a sound pressure of the sound to be output from the sound output unit reaches a certain value or higher after establishment of a telephone connection corresponding to the incoming call.

16. The electronic device according to claim 11, wherein the controller is configured to inactivate the first sensor when the execution of the phone call function is terminated.

17. The electronic device according to claim 11, wherein the controller is configured to inactivate the first sensor when a call ending operation to terminate a phone call using the phone call function is received from the user.

18. The electronic device according to claim 11, wherein the controller is configured to inactivate the first sensor when a telephone connection is relieved by a call partner using the phone call function.

19. The electronic device according to claim 11,
wherein the controller is configured to when the phone call function is not, in execution, inactivate the first sensor, and when the phone call function is, in execution and after establishment that a telephone connection corresponding to an outgoing call is started, supply power to the first sensor.

20. A control method executed by an electronic device used for a phone call, the method comprising: determining whether a phone call function is in execution; activating, when it is determined that the phone call function is in execution, a first sensor for detecting a substance contained in a first gas and a second sensor for detecting the substance contained in a second gas, and removing an influence of the substance contained in the second gas from a detection result of the first sensor based on a detection result of the second sensor, wherein the second sensor is provided on a face, of predetermined faces of the electronic device, different from a face where the first sensor is provided.

21. The control method according to claim 20, further comprising: acquiring a detected value of the second sensor on a back face side of the electronic device, acquiring a detected value of the first sensor on a front face side of the electronic device, and subtracting the detected value of the second sensor from the detected value of the first sensor.

22. A non-transitory storage medium that stores a control program that causes, when executed by an electronic device used fora phone call, the electronic device to execute: determining whether a phone call function is in execution; and activating, when it is determined that the phone call function is in execution, a first sensor for detecting a substance contained in a first gas and a second sensor for detecting the substance contained in a second gas, and removing an influence of the substance contained in the second gas from a detection result of the first sensor based on a detection result of the second sensor,
  wherein the second sensor is provided on a face, of predetermined faces of the electronic device, different from a face where the first sensor is provided.

23. An electronic device, comprising: a sound input unit; a first sensor provided near the sound input unit and configured to detect a substance contained in a first gas; and a second sensor configured to detect the substance contained in a second gas around the electronic device; and a controller configured to remove an influence of the substance contained in the second gas from a detection result of the first sensor based on a detection result of the second sensor.

* * * * *